(12) United States Patent
Hancock

(10) Patent No.: US 9,333,034 B2
(45) Date of Patent: May 10, 2016

(54) ELECTROSURGICAL APPARATUS FOR RF AND MICROWAVE DELIVERY

(75) Inventor: Christopher Paul Hancock, Bath (GB)

(73) Assignee: CREO MEDICAL LIMITED, Chepstow (GB)

( * ) Notice: Subject to any disclaimer, the term of this patent is extended or adjusted under 35 U.S.C. 154(b) by 317 days.

(21) Appl. No.: 13/992,666

(22) PCT Filed: Dec. 7, 2011

(86) PCT No.: PCT/GB2011/001693
§ 371 (c)(1),
(2), (4) Date: Jun. 7, 2013

(87) PCT Pub. No.: WO2012/076844
PCT Pub. Date: Jun. 14, 2012

(65) Prior Publication Data
US 2013/0267943 A1    Oct. 10, 2013

(30) Foreign Application Priority Data
Dec. 10, 2010   (GB) .................................. 1021032.6

(51) Int. Cl.
*A61B 18/18*   (2006.01)
*A61B 18/14*   (2006.01)
(Continued)

(52) U.S. Cl.
CPC ........... *A61B 18/1815* (2013.01); *A61B 18/042* (2013.01); *A61B 18/1206* (2013.01);
(Continued)

(58) Field of Classification Search
CPC ...... A61B 18/04; A61B 18/042; A61B 18/08; A61B 18/10; A61B 18/12; A61B 18/1206; A61B 18/14; A61B 18/18; A61B 18/1815; A61B 2018/0019; A61B 2018/00601; A61B 2018/0063; A61B 2018/00779; A61B 2018/00785; A61B 2018/00827; A61B 2018/00892; A61B 2018/128; A61B 2018/1861; A61B 2018/1876
USPC .................. 606/33–41, 51–52, 169, 205–207
See application file for complete search history.

(56) References Cited

U.S. PATENT DOCUMENTS

| 5,438,302 | A  | * | 8/1995 | Goble ........................... 331/167 |
| 6,582,427 | B1 |   | 6/2003 | Goble et al. |

(Continued)

FOREIGN PATENT DOCUMENTS

| EP | 2 253 286 A1   | 11/2010 |
| JP | 2002-537938 A  | 11/2002 |
| WO | WO 00/53112 A2 | 9/2000  |

OTHER PUBLICATIONS

International Search Report and Written Opinion, PCT/GB2011/001693, dated Feb. 27, 2012.

(Continued)

*Primary Examiner* — Michael Peffley
*Assistant Examiner* — Khadijeh Vahdat
(74) *Attorney, Agent, or Firm* — Arent Fox LLP

(57) ABSTRACT

A control system for electrosurgical apparatus in which the energy delivery profile of both RF EM radiation and microwave EM radiation delivered to a probe is set based on sampled voltage and current information of RF energy conveyed to the probe and/or sampled forward and reflected power information for the microwave energy conveyed to and from the probe. The energy delivery profile for the RF EM radiation is for tissue cutting (without requiring a sharp blade) and the energy delivery profile for the microwave EM radiation is for haemostasis or sealing or coagulation or ablation of tissue. The RF EM radiation and microwave EM radiation may be applied separately or simultaneously.

27 Claims, 12 Drawing Sheets

(51) Int. Cl.
*A61B 18/04* (2006.01)
*A61B 18/12* (2006.01)
*H05B 6/80* (2006.01)
*A61B 18/00* (2006.01)

(52) U.S. Cl.
CPC ......... *H05B6/806* (2013.01); *A61B 2018/0019* (2013.01); *A61B 2018/0063* (2013.01); *A61B 2018/00601* (2013.01); *A61B 2018/00779* (2013.01); *A61B 2018/00785* (2013.01); *A61B 2018/00827* (2013.01); *A61B 2018/00892* (2013.01); *A61B 2018/128* (2013.01); *A61B 2018/1861* (2013.01); *A61B 2018/1876* (2013.01)

(56) References Cited

U.S. PATENT DOCUMENTS

| | | |
|---|---|---|
| 2006/0155270 A1 | 7/2006 | Hancock et al. |
| 2008/0015575 A1* | 1/2008 | Odom et al. ............... 606/51 |
| 2008/0228179 A1* | 9/2008 | Eder et al. ............... 606/33 |
| 2010/0082083 A1 | 4/2010 | Brannan et al. |
| 2010/0286686 A1* | 11/2010 | Hancock ............... 606/33 |
| 2010/0296977 A1 | 11/2010 | Hancock |

OTHER PUBLICATIONS

Japanese Office Action mailed Jan. 20, 2015 for corresponding Japanese Patent Application No. 2013-542601.

* cited by examiner

ELECTROSURGICAL APPARATUS FOR RF AND MICROWAVE DELIVERY

CROSS-REFERENCE TO RELATED APPLICATIONS

This application is a National Stage entry of International Application No. PCT/GB2011/001693, filed Dec. 7, 2011, which claims priority to United Kingdom Patent Application No. 1021032.6, filed Dec. 10, 2010. The disclosures of the prior applications are hereby incorporated in their entirety by reference.

TECHNICAL FIELD

The invention relates to electrosurgical apparatus in which radiofrequency and microwave frequency energy is used to treat biological tissue. In particular, the invention relates to surgical apparatus capable of generating radiofrequency (RF) energy for cutting tissue and microwave frequency energy for haemostasis (i.e. sealing broken blood vessels by promoting blood coagulation), and/or, in conjunction with a flow of gas, using the RF energy and microwave frequency energy to strike and sustain a plasma, which may be used for cutting or sterilising tissue.

BACKGROUND TO THE INVENTION

Surgical resection is a means of removing sections of highly vascular organs from within the human or animal body, such as the liver or the spleen. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting.

For example, the Hemostatix® Thermal Scalpel System (http://www.hemostatix.com) combines a sharp blade with a haemostatic system. The blade is coated with a plastic material and connected to a heating unit which controls the temperature of the blade. The intention is for the heated blade to cauterise the tissue as it is cut.

Other known devices that cut and stop bleeding at the same time do not use a blade. Some devices use radiofrequency (RF) energy to cut and/or coagulate tissue. Other devices, for example the harmonic scalpels, use a rapidly vibrating tip to cut tissue and can provide a degree of coagulation.

The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell, that cannot be controlled by the cell membrane, resulting in the cell rupturing. When this occurs over a wide area it can be seen that tissue has been transected.

Whilst the above principle works elegantly in lean tissue, it is less efficient in fatty tissue because there are fewer ionic constituents to aid the passage of electrons. This means that the energy required to vaporise the contents of the cells is much greater, as the latent heat of vaporisation of fat is much greater than that of water.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured and changes from a rod like molecule to a coil, which causes the vessel to contract and reduce in size, giving the clot an anchor point, and a smaller area to plug.

However, RF coagulation is less efficient when fatty tissue is present because the electrical effect is diminished. It can thus be very difficult to seal fatty bleeders. Instead of having clean white margins, the tissue has a blackened, burned appearance. In vascular organs such as the liver there is also the heat sink effect as large volumes of fluid are being perfused through the tissue.

In practice, a RF device may operate using a waveform with a medium crest factor that is midway between a cutting and coagulating output.

The liver is highly vascularised, and for patients with cancers elsewhere in the body, it often becomes a site of secondary cancer. Large tumours or areas affected by numerous smaller tumours have to be resected to stop the cancer spreading throughout the organ, the function of which may already be compromised due to the administration of chemotherapy agents. Due to the concentration of blood vessels in the liver, surgery there is normally associated with high volume blood loss requiring vast quantities of blood to be transfused. Once bleeding starts in the liver, it can be difficult to stop. An argon beam coagulator is one example of a known device that can be used to try to stop the bleeding—this device produces surface coagulation.

WO 2008/044000 discloses surgical resection apparatus adapted to simultaneously cut and seal highly vascularised tissue, such as the liver or spleen. The apparatus comprises a source of microwave radiation that is coupled to a surgical instrument having an antenna associated with a blade for cutting biological tissue, wherein the antenna is arranged to controllably deliver microwave energy from the source to a region where the blade cuts through tissue. The microwave energy can coagulate blood to effectively seal off the blood flow at the cutting region. WO 2008/044000 suggests the use of high microwave frequencies (e.g. 10 GHz or higher), which offer a particular advantage over the use of known lower microwave frequency systems and radiofrequency (RF) systems due to the limited depth of penetration of the energy by radiation and the ability to enable small sharp blade structures to radiate energy efficiently into the tissue to seal off blood flow by being able to produce uniform fields along the length of the blade whilst at the same time being capable of cutting through the tissue to remove sections of diseased or cancerous tissue.

Attention has also been paid to preventing bleeding by advance treatment, i.e. treating the tissue to seal blood vessels before transection. In one known device, two lines of RF energy emitting needles are inserted into the liver tissue to perform in-line sealing. Ideally the RF energy is sufficient to seal the tissue through the full thickness of the liver. The blood supply to the area being transected is thus effectively cut off. When the tissue is subsequently cut through with a blade, there is no bleeding.

Vessels up to 7 mm in diameter can also be sealed using RF energy in a device that can also apply pressure. The vessel is held in a clamping device (e.g. forceps or the like). Pressure exerted on the vessel causes the contents of the vessel walls to be pushed out laterally, whereby the outer wall and inner wall of one side approach the inner and outer wall of the other side.

Applying RF energy at this point denatures the collagen of the wall matrix, and it intermingles before being locked in place as the tissue is fully desiccated. When the pressure is released, the newly formed stricture stays in place, meaning that the vessel can be divided, by cutting through the vessel on the efferent side using a sharp blade or the like. New collagen growth takes place through the tangled mass, so the stricture stays in place.

U.S. Pat. No. 6,582,427 discloses an electrosurgery system arranged to generate both RF energy (typically having a frequency of 1 MHz) and microwave energy (typically having a frequency of 2.45 GHz) for operation in a cutting mode or a coagulation mode.

SUMMARY OF THE INVENTION

At its most general, the present invention proposes a control system for an electrosurgical apparatus in which the energy delivery profile of both RF energy and microwave energy delivered to a probe is set based on sampled voltage and current information of RF energy conveyed to the probe and sampled forward and reflected power information for the microwave energy conveyed to and from the probe. In particular, the control system may derive (i.e. extract or otherwise determine) from the sampled voltage and current information of RF energy information indicative of voltage amplitude and current amplitude of the RF energy (e.g. peak and average values). Similarly, the control system may derive (i.e. extract or otherwise determine) from the sampled forward and reflected power information of microwave energy information indicative of the delivered power amplitude. It may also be possible to derive from the sampled voltage and current information of the RF energy information indicative of a phase difference between the voltage and current components of the RF energy. Similarly, the control system may derive from the sampled forward and reflected power information of the microwave energy information indicative of a phase difference therebetween.

Herein, energy delivery profile may mean the shape of the waveform in terms of voltage/current and time for the RF energy and power level and time for the microwave energy. Control of the energy delivery profile permits a range of therapeutic applications to be realised.

Accordingly, the invention may provide electrosurgical apparatus for resection of biological tissue, the apparatus comprising: a radiofrequency (RF) signal generator for generating RF electromagnetic (EM) radiation having a first frequency; a microwave signal generator for generating microwave EM radiation having a second frequency that is higher than the first frequency; a probe arranged to deliver the RF EM radiation and the microwave EM radiation separately or simultaneously from a distal end thereof; a feed structure for conveying the RF EM radiation and the microwave EM radiation to the probe, the feed structure comprising an RF channel for connecting the probe to the RF signal generator, and a microwave channel for connecting the probe to the microwave signal generator; an RF signal detector for sampling current and voltage on the RF channel and generating therefrom a RF detection signal indicative of the current and voltage; a microwave signal detector for sampling forward and reflected power on the microwave channel and generating therefrom a microwave detection signal indicative of the microwave power delivered by the probe; and a controller in communication with the RF signal detector and microwave signal detector to receive the RF detection signal and microwave detection signal, wherein the controller is operable to select an energy delivery profile for the RF EM radiation and the microwave EM radiation based on the received RF detection signal and/or microwave detection signal, the energy delivery profile for the RF EM radiation being for tissue cutting and the energy delivery profile for the microwave EM radiation being for haemostasis or sealing or coagulation or ablation of tissue.

The system may thus be configured to provide further control over electrosurgical apparatus capable of emitting radiofrequency electromagnetic radiation for cutting biological tissue and microwave electromagnetic radiation for haemostasis or sealing or coagulation or ablation of tissue.

The controller may be operable to select an energy delivery profile either based on the received RF detection signal and/or microwave detection signal, e.g. in a real time responsive manner, or from list of one or more predetermined energy delivery profile associated with a known tissue effect. For example, a preset energy delivery profile for tissue cutting may comprise delivering continuous wave (CW) RF EM energy with a 400 V peak amplitude at a power level of 30 W. In another example, a preset energy delivery profile for coagulation may comprise delivering continuous wave (CW) microwave EM energy at a power level of 25 W.

More generally, to achieve tissue cutting in a dry environment, it may be necessary to deliver a 500 kHz continuous wave sinusoidal waveform with a peak voltage of amplitude 400 V and a power setting of 40 W, whereas to achieve tissue cutting in a wet environment, it may be necessary to deliver one or more bursts of 500 kHz energy with a peak voltage of 4000 V with a peak power of 200 W and a duty cycle of 10%, which may be set up in the form whereby the ON time is 10 ms and the OFF time is 90 ms. This kind of pulsed energy delivery profile may ensure that the energy is passed to the tissue rather than causing undesirable heating of the surrounding fluid. For efficient tissue coagulation in dry tissue, CW microwave power may be delivered into tissue at an RMS power level of 30 W. For coagulation in a wet environment, the microwave power may be pulsed, e.g. having a peak power of 100 W with a 30% duty cycle.

Other waveforms that produce desirable therapeutic tissue affects may include a combination of RF and microwave energy delivered in CW and pulsed formats similar to those described above. The RF and microwave energy may be delivered simultaneously where the microwave energy modulates the RF energy. For example, a 400 V peak 500 kHz CW RF profile may be modulated with a 10 W CW 5.8 GHz microwave signal to produce a degree of tissue coagulation during the resection process to reduce bleeding when an organ or a section of an organ is being removed.

The control system may comprise a dedicated measurement channel, for delivering energy (preferably microwave energy) at a low power level (e.g. 10 mW or less). The system may thus make available measurement signals from a channel that is not delivering therapeutic effects, i.e. the waveform or energy delivery into tissue may be controlled based on low power measurements made using a channel that is not involved in delivering therapeutic tissue effects. The measurement channel may be use the same source as the microwave channel. The system may be switchable so that microwave energy is delivered either through the measurement channel (in a "measurement mode") or through the microwave channel (in a "treatment mode"). Alternatively, the microwave channel may be switchable between a low power mode (for measurement) and a high power mode (for treatment). In this arrangement a separate measurement channel is not needed.

In the measurement mode, using the microwave channel, it may be desirable to transmit a low power signal, e.g. 10 mW (10 dBm) or less, in a continuous wave (CW) format and examine the reflected energy signal, from which phase and magnitude information that relates to the current state of the tissue or the type of tissue in contact with the probe may be extracted (e.g. by a microwave measurement signal detector for sampling forward and reflected power on the measurement channel and generating therefrom a microwave detection signal indicative of the magnitude and phase of microwave power delivered by the probe). This measurement information may be extracted at the same time as higher power RF energy, e.g. at 50 W (47 dBm) or more, is being delivered into the tissue to produce therapeutic effects. The measurement information may be used to determine the optimal RF energy delivery profile to use, to determine when it is necessary to deliver higher power microwave power, e.g. at 40 W (46 dBm), into tissue e.g. to coagulate a burst vessel.

The system may be configured to supply energy for cutting and coagulating tissue simultaneously (e.g. a mixed or blend mode) or may be operated independently, whereby the RF and microwave energy is delivered to the probe under manual user control (e.g. based on the operation of a footswitch pedal) or automatically based on measured phase and/or magnitude information from the RF and/or microwave channel. The system may be used to perform tissue ablation and cutting. In the instance where microwave and RF energy are delivered simultaneously, either or both RF and microwave energy returned to the respective generators may be used at high power or low power to control the energy delivery profile. In this instance, it may be desirable to take measurements during the OFF time when the energy delivery format is pulsed.

An advantage of making measurements of returned energy at a frequency that is significantly different, i.e. by at least four orders of magnitude, from the therapeutic energy, is that the energy from the source that is delivering the therapeutic effects can be effectively blocked (e.g. using filters) from entering the measurement channel. For example, to ensure the high power RF energy signal does not affect the low power microwave measurement system, a high pass or band-pass filter is included in the system and located at the input to the measurement channel. This filter will allow the low power microwave signal to be transmitted into the tissue and for the reflected microwave signal to be received at the detector, but will block the high power RF signal. It is desirable for the filter to have a sharp roll off, i.e. 60 dB to 80 dB per decade or more, to ensure as much of the RF energy as possible is rejected.

The measurement channel may comprise a separate low power transceiver (or a low power transmitter and a heterodyne receiver) for extracting the phase and/or magnitude information from the measurement signal. This unit may be switched in on the microwave channel when the high power microwave source is not in use.

In one embodiment, the invention may include a radiofrequency matching network for promoting efficient transfer of radiofrequency electromagnetic radiation into tissue. Thus, an energy delivery system may be provided in which fixed frequency sources are used to create the RF and microwave energy and in which variable element tuning is employed to match the RF energy into biological tissue. Information from the measurement channel may be used to determine the adjustment of tuning elements on either the microwave or RF channel (when tuning is included in the particular arrangement of the electrosurgical system) to provide dynamic power matching between the probe (energy delivery system) and the tissue, which ensures efficient and controllable energy transfer between the electrosurgical system and the biological tissue.

In a further development, the apparatus according to the invention may also possess the ability to strike and sustain plasma at a treatment site as part of a preferential return path for the radiofrequency electromagnetic radiation, i.e. once struck, the impedance of the plasma is low and provides the preferential return path for the RF current to flow. When using plasma to cut tissue, the tip of the applicator is close to the surface of the tissue, whereas when using RF energy to cut tissue, the applicator is in contact with the tissue. The plasma produced by the generator disclosed in this invention can also be used to coagulate and vaporise tissue, e.g. the distance between the distal end of the applicator and the surface of the tissue may be 0.5 cm to 1.5 cm to perform effective surface coagulation. Being able to supply a combination of microwave and RF energy enables a high level of control over the thermal or non-thermal plasma produced at the distal end of the applicator.

The system may include an energy transport structure arranged to transmit and receive microwave and RF signals to allow both RF and microwave energy to be transported along one single channel (cable assembly) to a single applicator (probe) and allow control signals at the RF and microwave frequencies of choice to be detected and passed to the controller, that forms a part of the electrosurgical system, to enable the RF and microwave energy delivered into biological tissue to be delivered efficiently and in a controlled manner.

The distal end of the probe may comprise a bipolar emitting structure comprising a first conductor spatially separated from a second conductor, the first and second conductors being arranged to act: as active and return electrodes respectively to convey the RF EM radiation by conduction, and as an antenna to radiate the microwave EM radiation. Thus, the system may be arranged to provide a local return path for RF energy, i.e. a low impedance route for RF energy to be transported between the first and second conductors, which is part of the probe. For example, the dielectric separating the conductors may provide a local return path, or a plasma may be generated in the vicinity of the conductors to provide the local return path. RF tissue cutting may be produced by a fixed dielectric material separating the first and second conductors, where the thickness of the dielectric material is small, i.e. less than 1 mm and the dielectric constant high, i.e. greater than that of air. This arrangement may provide the necessary preferential return path for the current to flow. As explained in more detail below, this arrangement may also be partially filled with air or a gas (or a mixture of gases) and contain gas feed pipes to allow air or gas to enter (and possibly leave) the structure to enable non-thermal plasma to be formed to sterilise tissue or for thermal plasma to be formed to perform surface coagulation/ablation or tissue cutting. Probes that are able to receive gas for the purpose of creating a plasma are disclosed in WO 2009/060213, which is also incorporated herein by reference. Alternatively, the gas feed pipes may also be used to deliver saline (or other fluid) to the treatment site.

The system may operate by "seeing" the applicator differently depending on whether RF or microwave energy is being delivered thereto. Thus, the RF channel (and in particular the RF tuner under the control of the controller) may treat the applicator as a lumped element, e.g. a capacitor analysed using conventional circuit theory. In contrast, the microwave channel may treat the applicator as a distributed element modelled using EM field analysis and appropriate field simulation tools. As discussed below, the microwave channel may have its own tuner (e.g. impedance adjustor) or may be pre-matched with the impedance of the antenna. The RF tuner may be a means of adjusting the voltage and current being delivered into tissue to ensure efficient tissue cutting occurs in both a dry and wet environment.

As mentioned above, the feed structure may comprise a network that enables both RF and microwave energy to be delivered along a single channel into the applicator. In this situation, the RF channel and microwave channel may comprise physically separate signal pathways from the RF signal generator and microwave signal generator respectively, the separate signal pathway on the RF channel being isolated from the microwave EM radiation and the separate signal pathway on the microwave channel being isolated from the RF EM radiation. The isolation may be provided by a suitably configured low pass filter on the RF channel and a suitably configured high pass filter on the microwave channel.

Where there are separate channels, the feed structure may include a combining circuit, e.g. a signal combiner or duplexer-diplexer unit, having a first input connected to the separate signal pathway on the RF channel, a second input connected to the separate signal pathway on the microwave channel, and an output connected to a common signal pathway for conveying the RF EM radiation and the microwave EM radiation separately or simultaneously to the probe along a single channel. For example, a bi-directional diplexer or a duplexer-diplexer circuit may be used. The signal combiner (e.g. bi-directional diplexer) may be implemented as an open microstrip circuit. A low pass filter and/or a high pass filter may be integrated in the microstrip circuit to prevent the microwave EM radiation from leaking out of the first input and to prevent the RF EM radiation from leaking out of the second input, respectively. In one embodiment the signal combiner may comprise a switching device, e.g. a relay switch arrangement or coaxial switch arrangement, that connects either the RF channel or the microwave channel to the probe. In this embodiment the RF EM radiation and microwave EM radiation are kept separate from one another. The switching device may be arranged to alternate rapidly, whereby the probe receives alternating short bursts of RF EM radiation and microwave EM radiation. Such a signal may be regarded as quasi-simultaneous.

With this arrangement, the RF channel and microwave channel may share a common portion. The signal combiner may be arranged to receive signals at two separate frequencies (i.e. the RF frequency energy and the microwave frequency energy) and output them (either added together or separately) from a single output channel (e.g. cable assembly, such as a co-axial cable, waveguide assembly (flexible/twistable) or twisted pair,). The signal combiner may operate in both directions, i.e. it may enable forward signals (from RF and microwave energy sources) to travel to the probe, and may permit signals containing information concerning reflected energy to travel in the reverse direction for the purpose of signal measurement and system control, i.e. to discern information concerning the biological tissue in contact with the radiating section of the surgical antenna, or to control the dosage of energy being delivered into the biological tissue, i.e. to leave a safe margin. The information may be used to initiate a power reduction, i.e. from 100% to 10% in a short duration of time, i.e. 1 ms, to prevent unwanted damage occurring at the treatment site. The information that travels back to the generator is processed by the controller e.g. to detect the magnitude (voltage, current, forward or reflected power) and/or phase of the reflected signal compared with the forward going signal. This information may be used to control the system, e.g. to ensure that the power delivered into tissue is the same as the power level demanded by the user and/or to perform conjugate matching to ensure the power available at the source is the same as that delivered into the tissue load (less system losses, i.e. insertion loss of the cable assembly and probe, etc).

The apparatus may possess a dynamic RF tuner that operates by adjusting the reactance (inductance and/or capacitance) of a lumped element tuning network. The purpose of the RF tuner is to create a matching network in which the bulk impedance of the apparatus (seen at the distal end of the probe) is the complex conjugate of the tissue impedance. When matching occurs, the transfer of power into tissue and hence the efficiency of the tissue cutting function/action, may be maximised/optimised. The principle of matching in the invention may be based on matching a notional series RLC circuit with a notional parallel RLC in which the series reactance and the parallel reactance are adjustable and in which the series resistance represents the real part of the apparatus impedance and the parallel resistance represents the real part of the tissue impedance. By tuning the reactance itself, the apparatus may be operated using a fixed frequency source, which may improve signal stability and overall control.

The signal combiner may allow the RF and microwave signals at separate (i.e. non-contiguous) frequencies to be transmitted from a single port (diplexer action) towards the probe either separately or simultaneously. Preferential tissue effects may be produced by delivering energy at two different frequencies at the same time, i.e. the field from one source may add constructively or destructively to produce enhanced tissue effects. These may include: simultaneous cutting and coagulation to instantly stem bleeding of burst blood vessels during a resection procedure, or high amplitude pulses (or pulse trains) to enable efficient cutting/coagulation in wet environments, where lower amplitude CW waveforms may only cause fluid heating to occur.

In one example, the RF channel may comprise a RF power source coupled to the signal combiner, which may include a low pass filter to prevent the high frequency microwave energy from going back into the lower frequency RF power source and a high pass filter to prevent the lower frequency RF energy from going back into the higher frequency microwave energy source, which may otherwise cause damage to the output stage transistors used in the design of both RF and microwave sources.

The device may be used in general surgery (open or laparoscopic) where the voltage and/or current information from the RF stage and the reflected and/or forward power information from the microwave stage is used to control the energy delivery profiles produced by the RF and microwave energy delivery stages. For example, if the return loss measured on the microwave channel is between −6 dB and −10 dB (measured using the low power microwave transceiver during the RF cutting process), the controller may recognise the microwave detection signal to be indicative of a bleed. In response, the microwave source may be turned on and the microwave power level and/or duty cycle increased until the bleed has been stemmed (as indicated by a change in the return loss measured from the reflected signal on the microwave channel and/or the voltage/current information from the RF stage). The indication of the onset of a bleed may also be provided by voltage/current information (e.g. peak and average values) measured using the RF stage during the cutting process. In this instance, once the change in measured voltage/current that indicates a bleed is measured, the RF energy may be backed off and the microwave energy increased until the blood flow has been successfully stemmed. It may be preferable to deliver RF and microwave energy simultaneously, wherein one energy source is operating in the low power measurement mode and the other source is causing therapeutic tissue effects as well as providing measurement information, in order to provide more information to the controller to enable the controller to make the necessary adjustment of the energy delivery profile. The low power tissue measurements may be made during the OFF time when a pulsed waveform is being delivered to produce therapeutic tissue affects. Alternatively, the CW energy delivery waveform may be interrupted whilst tissue state measurements are being performed.

The invention may be particularly suitable in gastrointestinal (GI) procedures, e.g. to remove polyps on the bowel, i.e. for endoscopic sub-mucosal resection. The invention may also lend itself to precision endoscopic procedures, i.e. precision endoscopic resection, and may be used in ear, nose and throat procedures and liver resection.

The signal detector may comprise independent detectors for the RF and microwave EM radiation. An output from an RF signal detector only may be used to control the adjustable reactance of the RF tuner. The RF signal detector may be on the RF channel, and may be arranged to measure voltage and current of RF EM radiation on the RF channel (from which the RF detection signal indicative of amplitude (e.g. both peak and average) and/or phase may be extracted and used to control the energy delivery source). The RF signal detector may be arranged to communicate RF signal information that is indicative of the voltage and current of the RF EM radiation and a phase relationship between the voltage and current to the controller, the controller being arranged to vary the adjustable reactance of the RF tuner based on that RF signal information. The relationship between the voltage and current can be measured in terms of phase difference and this information may be used to indicate when the matched condition occurs or resonant point is achieved, i.e. when the phase difference is 0° the voltage and current are in phase, which implies that the capacitive reactance is equal in magnitude, but opposite in sign to the value of the inductive reactance, i.e. $-j\omega C = +j\omega L$, where C is capacitance in Farads, L is inductance in Henrys and $\omega = 2\pi f$, where f is frequency in Hertz, the resonant frequency thus being $$f = \frac{1}{2\pi\sqrt{LC}}.$$

In the tuning arrangement disclosed here, the resonant frequency is the operating frequency of choice, i.e. 100 kHz or 500 kHz, and so the values of L and C are adjusted in order to maintain the resonance point even when the values of tissue load vary during the tissue cutting process. The controller may be implemented using an analogue solution, in which signals proportional to the voltage and current of the RF EM radiation are input to a phase comparator to generate a signal proportional to the phase difference between the voltage and current. The controller may comprise a self-adjusting feedback loop arranged to dynamically vary the adjustable reactance to minimise the phase difference. Alternatively, the signals proportional to the voltage and current of the RF EM radiation and the signal proportional to the phase difference between the voltage and current may be conditioned (e.g. voltage clamped, filtered and/or rectified) to be suitable as input signals for a microprocessor or microcontroller. The controller may thus comprise a microprocessor arranged to receive the RF signal information, determine an adjustment to the adjustable reactance, and generate and output one or more control signals for causing the adjustment.

The RF signal detector may be arranged to measure voltage and current on the RF channel at an input and/or an output of the RF tuner or at an RF output transformer that may form an output stage of the RF power source. The voltage may be measured using either a resistive or reactive potential divider or by taking a winding off (tapping off) the primary or secondary of the RF output transformer or by including a separate winding on the primary side of the transformer. Preferably, the RF signal detector may include a potential divider comprising a pair of reactive elements (e.g. capacitors or coils) arranged to permit measurement of RF signal information that is indicative of the voltage of the RF EM radiation. This has the advantage of potentially being virtually lossless arrangement (although of course there will always be some loss due to the equivalent series resistance (ESR) of the capacitor, but this will be negligible as long as a low loss dielectric is used).

Furthermore, the adjustable reactance of the RF tuner may comprise the total reactance of the pair of reactive elements. In other words, the RF tuner and RF signal detector may share common components. The total reactance of the pair of reactive elements may be variable to assist the function of the RF tuner, whilst the ratio between the reactances of the pair of reactive elements is maintained to provide the function of the substantially lossless potential divider.

The RF signal detector may include a current transformer on the RF channel to permit measurement of RF signal information that is indicative of the current delivered into tissue. The current transformer (CT) will be in series with the output (on the primary or secondary side of the RF output transformer) and may comprise a small toroidal core made from packed iron dust or ferrite, a single turn of wire as the primary winding of the CT, multiple turns of wire as the secondary winding of the CT and a burden resistor across the secondary winding.

The adjustable reactance may include a first variable reactance connected in series on the RF channel and a second variable reactance connected in parallel with the RF channel. The first variable reactance may be purely inductive or capacitive. The second variable reactance may be purely inductive or capacitive. Preferably the first variable reactance is inductive and the second variable reactance is capacitive and incorporates the potential divider mentioned above. The variable parallel reactance may be connected before or after the variable series reactance. Alternatively, a variable (or fixed) shunt connected reactance may be connected before and after the variable series reactance (provides an alternative tuning arrangement or filter design). A variable capacitance may be achieved by varying the distance between the plates of a parallel plate capacitor, by varying the value of relative permittivity (or dielectric constant) of the material between the two plates (e.g. by applying an electric field to the material), by varying the surface area of the plates, i.e. by sliding a moveable plate over a fixed plate with air or a dielectric material separating the plates, by creating plasma between the two plates and switching the plasma on and off, or by movement of the vanes of the rotary variable capacitor.

A composite effect may be obtained by using a sheet of material to separate the two plates that has a non-uniform dielectric constant over the area of the sheet (or a distribution of dielectric constants over the area of the sheet created by fabricating the sheet out of individual sections of material with various dielectric constants) and fixing this sheet of material to one metallic plate whilst varying the area over which a second metallic plate makes contact with the dielectric material/first plate. A further variation could be obtained by varying the distance of separation between the plate with the sheet of non-uniform dielectric constant material deposited and the sheet that moves over the first plate.

A variable inductance maybe achieved by moving a magnetic material with a relative permeability of greater then unity in and out of a linear coil winding, by varying the relative permeability of a material contained within an inductive coil of wire, by varying the number of turns of wire on an inductive coil by shorting or switching turns in and out, by varying the cross sectional area of the coil, or by opening and closing windings of a linear coil, i.e. by varying the length of the coil to increase or decrease the distance between adjacent windings or turns of wire. The equation that governs how the inductance L varies when changing the abovementioned parameters is $$L = \frac{\mu_0 \mu_r N^2 A}{l},$$

where $\mu_0$ is the permeability of free space, $\mu_r$ is the relative permeability, N is the number of turns of wire, A is the cross sectional area (m$^2$) and l is the length of the inductive coil (m). A control signal for the variable capacitance or variable inductance may be derived from the self-adjusting feedback loop mentioned above.

Alternatively or additionally, each of the first and second variable reactances may comprise a plurality of reactive elements, each reactive element having a fixed reactance and being independently switchable into or out of connection with the RF channel according to a respective control signal from the controller, i.e. electronically controlled switches may be used to short out a single turn or multiple turns of wire that form an inductive coil or to short out the parallel plates of banks of capacitors arranged in a parallel or series configuration. This arrangement may be suited to the use of a digital controller. That is, the controller may comprise a digital microprocessor programmed to determine a state for each of the respective control signals based on the RF signal information from the signal detector and output the respective control signals corresponding to those determined states.

To ensure that the power available from the RF source is delivered efficiently into the tissue load, a shunt capacitance (fixed or variable and adjusted manually or automatically) may be connected across the primary or secondary coil of the RF output transformer to perform power factor correction, where the difference in phase between the voltage and the current at the load is corrected for, i.e., reduced to a minimum value (ideally, the voltage and current waveform should be in phase), by introducing a reactance to shift the phase of the voltage or current. The phase difference between the voltage and current depends upon the load and so this can be corrected for dynamically by varying the value of capacitance using one of the methods discussed above. Preferably, the capacitance is adjusted so that voltage and current are in phase.

The RF channel may comprise an RF signal generator having any suitable arrangement for outputting an RF signal with a stable frequency suitable for tissue cutting. For example, the RF signal generator may comprise an oscillator (e.g. a Clapp oscillator) for generating stable RF oscillations which are subsequently amplified by an RF amplifier. To facilitate amplification, the oscillator may be arranged to drive a switching unit to generate a stable RF pulsed signal. The amplifier may be arranged to amplify the RF pulsed signal. The amplifier may include a transformer, wherein the switching unit is arranged to switch rapidly ON/OFF a voltage across a primary coil of the transformer. The switched voltage may represent the RF pulsed signal. A secondary coil of the transformer may be arranged to output an amplified version of the RF pulsed signal. However, the transformer need not provide an amplifying function. It may provide DC isolation between the generator and the user, i.e. form a galvanic or DC isolation barrier. The amplifier may include (additionally or alternatively to the transformer) a single-ended or push pull or half bridge or full bridge arrangement, e.g. implemented using power MOSFETs, bipolar junction transistors (BJTs), insulated gate bipolar transistors (IGBTs) or the like.

If the oscillator and amplifier arrangement operates to generate an RF pulsed (e.g. square wave) signal, the signal generator preferably includes a low pass filter for extracting a single sinusoidal output from the switched or square wave signal at the fundamental frequency, i.e. the harmonics, e.g. $3^{rd}$, $5^{th}$, $7^{th}$, etc, to produce a square wave are removed. The extracted sinusoidal output may represent the RF EM radiation output from the signal generator to the feed structure. In one embodiment, the RF EM radiation comprises a peak-to-peak voltage of 200-400 V delivered in a continuous wave format at 500 kHz.

The signal detector may comprise a reflected microwave signal detector on the microwave channel for measuring the microwave EM radiation conveyed between the probe and the microwave signal generator, the microwave signal detector being arranged to communicate microwave signal information that is indicative of the magnitude and/or phase of reflected microwave EM radiation to the controller, the controller being arranged to vary the adjustable reactance of the tuner based on that microwave signal information. If the tuner is not included in the system, then the voltage or current or power levels may be increased up to their maximum values on both RF and microwave channels, i.e. if the demand for the power at the tip of the probe is 50 W and the reflected power (taking into account cable and probe losses) is 30 W, this implies the power at the probe tip is 20 W, so the power at the amplifier has to be increased by 30 W in order to produce the desired 50 W at the probe tip. If the insertion loss of the cable and probe equates to 25 W, this implies that the power required from the source to deliver 50 W into tissue is 105 W.

Optionally, the microwave channel may comprise a tuneable portion for matching the impedance of the microwave channel line-up of the apparatus with the load seen at the distal end of the probe. Accordingly, the microwave channel may comprise an impedance adjuster connected on the microwave channel between the microwave signal generator and the probe, the impedance adjuster having an adjustable complex impedance that is controllable based on the detected phase and/or magnitude of the reflected and/or forward going microwave radiation. The signal detector may further comprise a forward microwave signal detector on the microwave channel for measuring the microwave EM radiation conveyed between the microwave signal generator and the probe. An arrangement corresponding to that disclosed in WO 2008/044000 may be used. For example, the impedance adjuster may comprise one or more tuning stubs, power varactor or PIN diodes or a single varying length microstrip or stripline or co-axial line tuning stub that is moved along a microstrip, stripline or co-axial line, wherein the movement along the line and the variation in the length of the tuning stub is up to a half wavelength at the frequency of the microwave EM radiation.

Measurements of the magnitude and/or phase information of the forward and reflected microwave EM radiation may be made using an integrated microwave transceiver, such as the MAX2829ETN made by Maxim Integrated Products. An advantage of this approach is that a separate local oscillator signal may not need to be generated independently for mixing down the frequency of the detected microwave EM radiation. The integrated transceiver may also be used to generate the source frequency for the microwave power amplifier, i.e. at 5.8 GHz or 14.5 GHz. A separate transceiver may be used to measure forward and reflected radiation or the same transceiver integrated circuit may be configured to perform this function by switching in and out separate channels. The microwave transceiver may be arranged to receive inputs from one or more directional couplers arranged to couple a fixed percentage, i.e. 1% or 10%, of the forward or reflected microwave EM radiation on the microwave channel and output I (in-phase) and Q (quadrature phase) signals representative of magnitude and phase information of the reflected and/or forward microwave EM radiation at a low enough frequency, i.e. 10 MHz, that can be used by a standard Analogue to Digital Converter that forms part of a DSP unit or a standard microcontroller, which in turn are representative of the state of the biological tissue in contact with the distal end of the probe. The impedance adjuster may be controlled by the controller on the basis of the output I and Q signals. The impedance adjuster may be a waveguide tuner that contains one or more mechanical tuning stubs or rods that may be made from a metallic or dielectric material. These rods are moved into and out of a waveguide cavity in order to match the impedance of the biological tissue with the impedance of the radiating applicator (or antenna).

The first frequency may be a stable fixed frequency in the range 10 kHz to 300 MHz and the second frequency may be a stable fixed frequency in the range 300 MHz to 100 GHz. The first frequency should be high enough to prevent the energy from causing nerve stimulation and low enough to prevent the energy from causing tissue blanching or unnecessary thermal margin or damage to the tissue structure. Preferred spot frequencies for the first frequency include any one or more of: 100 kHz, 250 kHz, 500 kHz, 1 MHz, 5 MHz. Preferred spot frequencies for the second frequency include 915 MHz, 2.45 GHz, 5.8 GHz, 14.5 GHz, 24 GHz.

As mentioned above, where RF EM radiation and microwave EM radiation may be supplied to the probe simultaneously, they may be used in a complementary fashion to create a plasma that may assist with the cutting function and/or the sealing function and/or sterilisation function of the apparatus. In particular, the RF channel may be configured to generate a high voltage EM field at the distal end of the probe that is suitable for striking a plasma, which can be subsequently sustained by the microwave EM radiation. The distance between the two plates (or the two co-axially arranged conductors in a co-axial based applicator) may be such that the electric field (V/m) set up between the two plates (or other conductor arrangement) by the microwave field is high enough to strike and maintain the plasma. By providing a controlled flow of gas (e.g. air or an inert gas, such as argon) in this region, controllable plasma may be struck and sustained. The plasma generated to provide a local return path for RF currents may be thermal or non-thermal plasma.

Accordingly, the apparatus may comprise a gas feed connected to supply a flow of gas to the distal end of the probe, wherein, if the flow of gas is present, the RF EM radiation is adjusted to strike a conducting gas plasma between the first and second conductors at the distal end of the probe and the microwave EM radiation is arranged to sustain the gas plasma. In certain instances, only the RF or microwave field may be needed.

Locally generating a plasma in a controlled manner between the first and second conductors of the probe offers advantages in terms of reliability and control of the RF energy distribution, i.e. in conventional system saline is often used to create the return path or the path of conduction between the active and return electrodes in a bipolar arrangement. This can be unreliable, messy and often impractical to implement.

The probe used with the system of the invention comprises a bipolar antenna rather than a monopolar arrangement. Monopolar RF systems are undesirable for the following reasons:
 the patient forms a part of the return path, which can lead to a burn or damage to healthy tissue at sites other than the treatment site,
 the voltages required are higher than those needed using bipolar apparatus, i.e. 4 kV peak compared to 400 V peak,
 the external pad or plate required with a monopolar system may come disconnected from the patient and so the energy delivery into tissue is interrupted or completely stops, and
 when the tissue becomes charred, the current stops flowing through the tissue and so tissue cutting or ablation or coagulation or desiccation ceases. Monopolar operation is particularly undesirable in gastrointestinal procedures due to the RF current needing to pass through the bowel wall, which can cause perforation. Also the inability to control the energy delivery into sensitive thin walled structures, such as the bowel, is highly undesirable. The self-contained plasma return path of the invention offers significant benefit when the device is used in regions of the body that are difficult to access.

The bipolar emitting structure of the probe may comprise an antenna structure in which the gas is piped out of an outlet at the distal end of the probe or the structure may contain two pipes connected to the same end as where the microwave/RF energy enters the structure, i.e. the proximal end. In this arrangement the gas conduit and outlet may be integrated into the probe structure. In the closed or sealed arrangement, a first pipe may be used to feed the gas into the structure and a second pipe used for extraction or recycling, i.e. the gas may also be circulated around the circumference of the probe or between the conductors and returned to the second inlet port, i.e. the gas is circulated in a closed system. The gas pressure and/or outlet configuration may be arranged to create a line of plasma along an edge of the probe at the distal edge of the probe. The probe may partially or fully enclose the plasma, which may ensure that it is sustained in all tissue environments. Where the plasma is partially or fully exposed to biological tissue, it may assist the cutting action or be used to perform surface coagulation (if it is a thermal plasma) or sterilize the tissue (if it is a non-thermal plasma), thus the probe could be used in three modes of operation, namely: to cut tissue, to coagulate or ablate tissue and to sterilise tissue. The device may also be used to cause shrinkage of vessel walls.

In one embodiment, the bipolar emitting structure may comprise a planar block of dielectric material (e.g. ceramic or quartz), the first and second conductors being conductive layers provided on opposite surfaces of the planar block. This structure may present a single edge at the distal end of the probe that comprises a pair of conductive lines separated by a dielectric material. This edge may represent the "cutting" edge of the instrument. The edge may be blunt, e.g. rounded, to avoid accidental or unwanted physical slicing of tissue.

The conducting gas plasma may be used to address problems associated with conventional monopolar RF electrosurgical systems, where the patient's body forms a part of the circuit and the currents (displacement) passes through the body. For this to work, the patient must be attached to the ground or a return path, e.g. via a pad that may be attached to patient or via a conductive sheet that the patient may lie on. These conventional systems may cause local burns if the patient is only partially connected or inefficient RF energy coupling into tissue.

The ability of the system to sterilise may be particularly useful when the structure is inserted via a natural orifice, i.e. mouth, urethra, anus (which may contain bacteria) then through an internal incision in the stomach, vagina, bladder or colon (which may also contain bacteria)—this surgical technique is known as Natural Orifice Transluminal Endoscopic Surgery (NOTES). These structures may also be useful for use in Transanal Endoscopic Microsurgery (TEMS), which is a relatively painless method of removing abnormal rectal growths. This treatment requires no incision to be made and is suitable for the treatment of certain early stage rectal cancers or benign rectal polyps. These structures may also be useful for carrying out single port laparoscopic surgery, which is surgery performed through a single port or incision made in a patient's navel and is a form of minimally invasive laparoscopic surgery, but where only one incision is made.

Ionisation discharge between the first and second conductors caused by the RF or microwave field in combination with an inert gas (or air) may be sufficient to produce the necessary tissue sterilisation effect. RF or microwave generated plasma alone may be sufficient to produce the tissue cutting effect.

The present invention may thus permit a combination of RF energy, microwave energy and gas (or air) to be used to create the non-thermal plasma, thermal plasma, RF tissue cutting, tissue coagulation, tissue ablation, tissue sterilisation, or surface coagulation.

In one aspect of the invention, the apparatus may be used to cut through blood vessels. In this aspect, the combination of the microwave and RF energy delivered from a common instrument is used to apply microwave energy before the RF energy in order to coagulate blood in the vessel so that it is effectively sealed before the RF cutting energy is applied. In this aspect, the microwave and RF energy may be delivered from the probe into tissue in such a manner that the microwave energy (e.g. for coagulation) initially penetrates (i.e. is effective in achieving coagulation or tissue parting) to a depth of 2x, following which the RF energy (e.g. for cutting) penetrates (i.e. is effective in achieving tissue separation) to a depth of x. It may be preferable to generate profiles of microwave and RF energy simultaneously to ensure the most efficient sealing effect is achieved, i.e. maintain the microwave sealing effect while the RF cutting takes place. It may be necessary to clamp and hold the vessel during the procedure.

This technique may be used with a probe having a single radiating edge (comprising the bipolar emitting structure), which may be used for example in open or key-hole (laparoscopic) device for cutting through highly vascularised tissue. Using these modes in combination (e.g. in series or simultaneously) may ensure a safety margin for blood-free cutting. A plug must be formed at the end of the vessel that creates a structure to ensures the vessel is permanently sealed. Alternatively, the first and second conductors may be provided on opposing surfaces of a clamp-like probe.

In summary, the apparatus disclosed herein may provide one or more of the following functions and advantages:
radiation of controlled and focussed microwave energy for efficient coagulation (to deal efficiently and effectively with large blood vessels and fatty tissue);
conduction of controlled and focussed RF energy for effective tissue cutting without the use of a sharp blade (produces thermal margins similar to those produced by a surgical blade);
a dynamic tuning configuration for the microwave and/or RF energy source to enable the energy to be focussed into the biological tissue, even when there is a dramatic change in tissue impedance (enables efficient energy transfer, efficient device operation and effective quantification of final tissue effects due to knowing exactly the dosage of energy delivered into tissue);
an infrastructure of components arranged to convey microwave and RF energy down a single cable structure in both forward and reverse directions to enable effective energy delivery for treatment mode and signal measurement mode for accurate system control;
an applicator structure (i.e. probe) that enables the microwave and RF energy to be combined and delivered into radiating/conductive elements contained at the distal end of the probe (lumped elements for RF energy and distributed elements for microwave energy), that are in contact with the target tissue and enable the RF and/or microwave energy to be efficiently coupled into the tissue;
introduction of gas into the probe to promote the generation of plasma that may be used to provide a local return path for the RF current and/or produce non-thermal plasma to sterilise tissue and/or produce thermal plasma to cut tissue and/or coagulate the surface of tissue.

In addition to the use on blood vessels discussed above, the invention may also be used to seal against the flow of air, e.g. in vessels in the lungs, where it may be desirable to seal air pockets.

The steps of operating the system discussed above may include:
introducing RF energy to strike a non-thermal or thermal plasma (preferably non-thermal);
introducing microwave energy to sustain the plasma (in practice, the microwave field and RF field may be applied simultaneously in the form of a pulse, where the leading edge of the microwave pulse triggers a shorter high voltage RE pulse to strike the plasma, i.e. 2 kV pulse for 100 µs within the window of a 30 W microwave pulse for 100 ms;
removing the RF energy (e.g. switching off the RF channel) while the plasma at the probe stabilises to set up low impedance path between the two conductors;
introducing RF energy suitable for tissue cutting, i.e. having a continuous wave waveform at a frequency of between 100 kHz and 500 kHz and peak to peak voltage of 400 V to cause tissue cutting or dissection to occur with the local return path set-up by the plasma or the local return set up by arranging the applicator as a parallel plate structure, with a small distance of separation between the plates, i.e. less than 1 mm and having a high permittivity material filling the gap between the plates.

The RF field may also be present for longer during the plasma strike, e.g. 10 ms rather than 100 µs, where it will be superimposed on top of the microwave field to produce preferential tissue effects such as argon beam coagulation, where controllable hot plasma is required to coagulate the surface of the tissue to, for example, treat ulcers or other growths that are on the surface of the tissue or to coagulate blood. In the instances where the RF and microwave fields are present, but plasma is not struck, i.e. where a gas is not present, or the distance between the conductors where the E-field is set up does not allow a plasma to be struck, the energy delivered into tissue will be non ionising energy suitable for cutting and coagulating, so the superimposed RF and microwave fields may produce a mixed mode effect, where vessels can be coagulated and cut simultaneously. The composite RF and microwave field may produce a dominant cut with some coagulation to prevent bleeding.

The invention described may be used with the electrosurgical probe disclosed in the applicant's earlier UK patent application no. 0912576.6, filed on 20 Jul. 2009, and incorporated herein by reference. UK patent application no. 0912576.6 describes an electrosurgical probe in the form of a spatula comprising a planar transmission line for carrying microwave energy formed from a sheet of a first dielectric material having first and second conductive layers on opposite surfaces thereof, the planar transmission line being connected to a coaxial cable that is arranged to deliver microwave energy to the planar transmission line, the coaxial cable comprising an inner conductor and an outer conductor with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The first conductive layer is spaced from the end of the transmission line that abuts the coaxial cable to electrically isolate the outer conductor from the first conductive layer, and the width of the first and second conductive layers is selected to create an impedance match between the transmission line and the coaxial cable. The spatula configuration set forth in UK patent application no. 0912576.6 provides desirable insertion loss between the co-axial feed line and the end radiating section, whilst also providing desirable return loss properties for the edges of the spatula when in contact with air and biological tissue respectively. The probe discussed in UK patent application no. 0912576.6 is intended to radiate microwave energy from the edges of the planar transmission line to cause localised tissue ablation.

UK patent application no. 0912576.6 also discloses that the spatula discussed above may have an RF cutting portion integrated therewith. The RF cutting portion may be formed by using the first and second conductive layers mentioned above as active and return electrodes for RF energy. This arrangement may take advantage of the fact that the active and return electrodes are in close proximity to one another, thus setting up a preferential return path to enable local tissue cutting action to take place without the need for a remote return pad or a highly conductive liquid, i.e. saline, existing between the two electrodes.

BRIEF DESCRIPTION OF THE DRAWINGS

Examples of the present invention are discussed in detail below with reference to the accompanying drawings, in which.

DETAILED DESCRIPTION

Further Options and Preferences

The apparatus described in the embodiments herein is for producing and combining focussed microwave and RF energy suitable for coagulating/sealing, cutting and sterilising biological tissue. The invention provides for control of the energy profile (e.g. power level and/or waveform) of RF and microwave EM radiation delivered into tissue based on detected signal information indicative of the nature of load i.e. biological tissue, at the distal end of the probe. Some embodiments discussed below also incorporate dynamic tissue matching techniques to ensure maximum energy delivery into tissue over a range of impedances that can vary from less than 10Ω to greater than 100 kΩ. The apparatus is preferably used with a probe that is configured to create a preferential return path for the RF cutting currents, and which enables effective surgical resection procedures to be carried out without blood loss using open access and minimally invasive (endoscopic, laparoscopic or key-hole) surgical techniques.

In particular, the embodiments present a new electrosurgical generator that can enable open and key-hole surgical resection, vessel sealing, NOTES, TEMS and other surgical procedures to be performed in a far more efficient and effective manner than can be achieved using currently available RF-, laser-, or ultrasonic frequency-based technologies. The apparatus may be particularly suited to gastrointestinal and ear, nose, throat procedures. The apparatus may be particularly suitable for use in performing endoscopic sub-mucosal resection (ESR) and other procedures relating to polyps or growths within the bowel.

Figure 1:
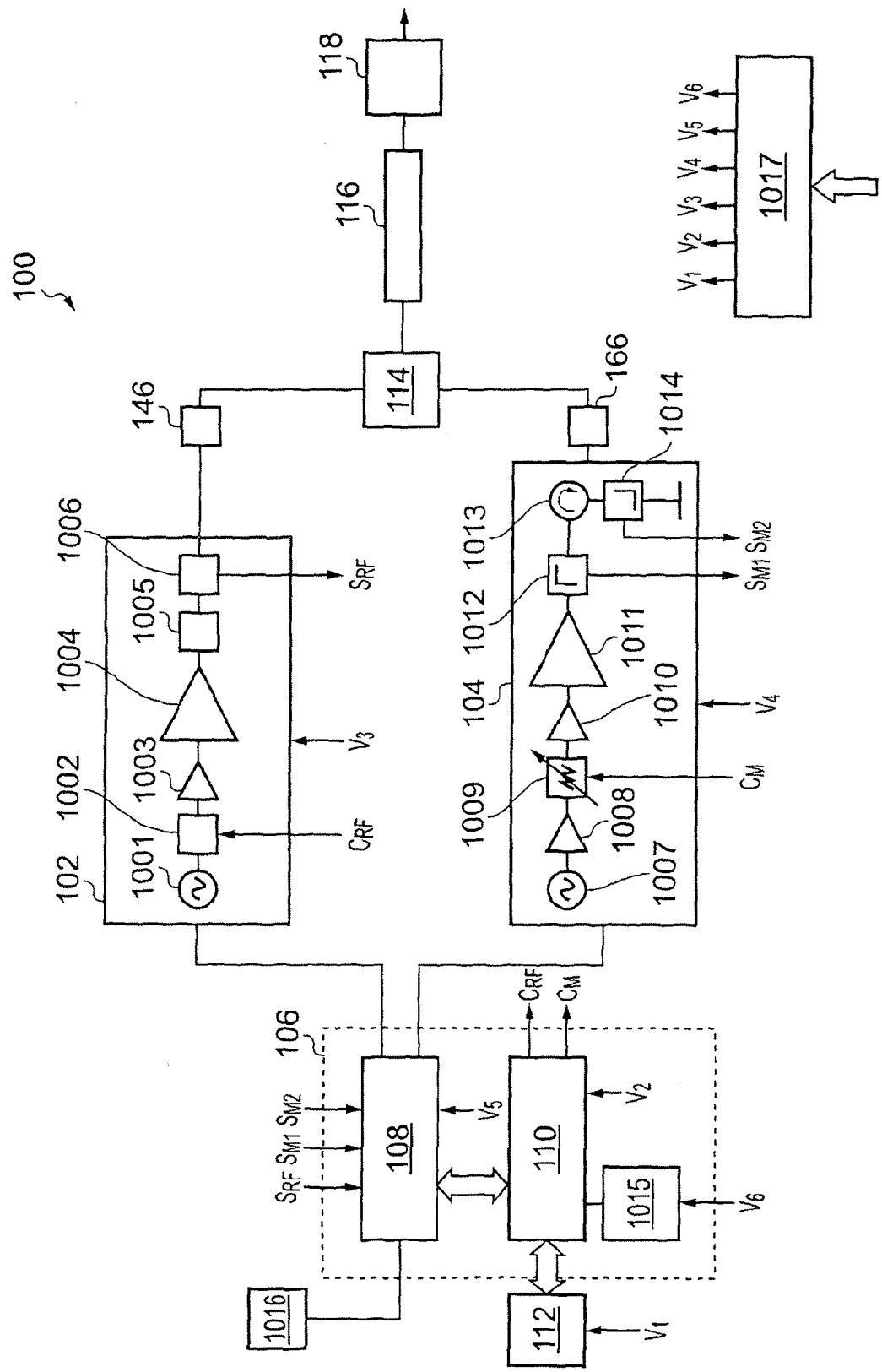
FIG. 1 is an overall schematic system diagram of electrosurgical apparatus according to an embodiment of the invention.

FIG. 1 shows an overall system diagram for an electrosurgical system 100 that is an embodiment of the invention. The system shown here may be used in any clinical or surgical procedure that involves: tissue cutting, tissue coagulation, tissue ablation, tissue desiccation and tissue sterilisation.

The system may be configured to produce hot and cool plasma for surface coagulation and tissue sterilisation respectively. Having these options available makes the system particularly suitable for applications involving NOTES, where the applicator is introduced into the body through a natural orifice.

The system 100 comprises an RF line-up 102 and a microwave line-up 104, which form parts of a RF channel and a microwave channel respectively.

The RF line-up 102 contains components for generating and controlling an RF frequency electromagnetic signal at a power level suitable for treating (e.g. cutting or desiccating) biological tissue. In this embodiment, it includes an RF oscillator 1001, a power controller 1002, an amplifier unit (here comprising a driver amplifier 1003 and a power amplifier 1004), a transformer 1005 and an RF signal detector 1006. Optionally, the RF line-up 102 includes a lumped element impedance matching sub-system, through with the reactance of the RF channel can be adjusted. This option is discussed below in more detail with reference to FIG. 2.

The microwave line-up 104 contains components for generating and controlling a microwave frequency electromagnetic signal at a power level suitable for treating (e.g. coagulating or ablating) biological tissue. In this embodiment it includes a phase locked oscillator 1007, a signal amplifier 1008, a adjustable signal attenuator (e.g. an analogue or digital diode attenuator) 1009, an amplifier unit (here a driver amplifier 1010 and a power amplifier 1011), a forward power coupler 1012, a circulator 1013 and a reflected power coupler 1014. The circulator 1013 isolates the forward signal from the reflected signal to reduce the unwanted signal components present at the couplers 1012, 1014, i.e. it increases the directivity of the couplers. Optionally, the microwave line-up includes an impedance matching sub-system having an adjustable impedance. This option is discussed below in more detail with reference to FIG. 2.

In this context, RF energy is defined as energy at a frequency of up to 300 MHz, i.e. 100 kHz, 500 kHz, 5 MHz, etc. and microwave energy as anything beyond 300 MHz, i.e. 2.45 GHz, 5.8 GHz, 24 GHz, etc.

The RF line-up 102 and microwave line-up 104 are in communication with a controller 106, which may comprise signal conditioning and general interface circuits 108, a microcontroller 110, and watchdog 1015. The watchdog 1015 may monitor a range of potential error conditions, which could result in the system not performing to its intended specification, i.e. the system delivers the wrong dosage of energy into patient tissue due to the output or the treatment time being greater than that demanded by the user. The watchdog 1015 comprises a microprocessor that is independent of the microcontroller 110 to ensure that microcontroller is functioning correctly. The watchdog 1015 may, for example, monitor the voltage levels from DC power supplies or the timing of pulses determined by the microcontroller 110. The controller 106 is arranged to communicate control signals to the components in the RF line-up 102 and microwave line-up 104. In this embodiment, the microprocessor 110 is programmed to output an RF control signal $C_{RF}$ and a microwave control signal $C_M$ for the power controller 1002 and the adjustable signal attenuator 1009 respectively. These control signals are used to set the energy delivery profile of the RF EM radiation and the microwave EM radiation output from the RF line-up 102 and microwave line-up 104 respectively. In particular, the power controller 1002 and the adjustable signal attenuator 1009 are capable of controlling the power level of the output radiation. Moreover, the power controller 1002 and the adjustable signal attenuator 1009 may include switching circuitry capable of setting the waveform (e.g. pulse width, duty cycle, etc.) of the output radiation.

The microprocessor 110 is programmed to output the RF control signal $C_{RF}$ and the microwave control signal $C_M$ based on signal information from the RF signal detector 1006 and forward and reflected power couplers 1012, 1014. The RF signal detector 1006 outputs a signal or signals $S_{RF}$ which are indicative of the voltage and current (and optionally the phase between the voltage and current) of the RF EM radiation on the RF channel. In this embodiment, the RF and microwave generator may be controlled by measurement of phase information only, which can be obtaining from either the RF channel (from sampled current and voltage information) or the microwave channel (from sampled forward and reflected power information). The forward power coupler 1012 outputs a signal $S_{M1}$ indicative of the forward power level and the reflected power coupler 1014 outputs a signal $S_{M2}$ indicative of the reflected power level. The signals $S_{RF}$, $S_{M1}$, $S_{M2}$ from the RF signal detector 1006 and the forward and reflected power couplers 1012, 1014 are communicated to the signal conditioning and general interface circuits 108, where they are adapted to a form suitable for passing to the microprocessor 110.

A user interface 112, e.g. touch screen panel, keyboard, LED/LCD display, membrane keypad, footswitch or the like, communicates with the controller 106 to provide information about treatment to the user (e.g. surgeon) and permit various aspects of treatment (e.g. the amount of energy delivered to the patient, or the profile of energy delivery) to be manually selected or controlled, e.g. via suitable user commands. The apparatus may be operated using a conventional footswitch 1016, which is also connected to the controller 106.

The RF and microwave signals produced by the RF line-up 102 and microwave line-up 104 respectively are input to a signal combiner 114, which conveys the RF and microwave EM radiation separately or simultaneously along a cable assembly 116 to the probe 118. In this embodiment, the signal combiner 114 comprises a duplexer-diplexer unit that allows energy at microwave and RF frequencies to be transmitted along cable assembly 116 (e.g. a coaxial cable) to a probe (or applicator) 118, from which it is delivered (e.g. radiated) into the biological tissue of a patient. In other embodiments, the signal combiner 114 may comprise a switching device such as a relay switch or coaxial switch which is capable of alternating the signal supplied to the probe 118 between the RF and microwave EM radiation. The switching device may have a switching speed suitable for rapidly alternating between the RF and microwave so that they are received at the probe 118 quasi-simultaneously. Examples of the probe 118 are discussed below.

The signal combiner 114 also permits reflected energy, which returns from the probe 118 along cable assembly 116, to pass into the microwave and RF line-ups 102, 104, e.g. to be detected by the detectors contained therein. As explained below, the apparatus may include a low pass filter 146 on the RF channel and a high pass filter 166 on the microwave channel, so that only a reflected RF signal enters the RF line-up 102 and only a reflected microwave signal enters the microwave line-up 104.

Finally, the apparatus includes a power supply-unit 1017 which receives power from an external source 1018 (e.g. mains power) and transforms it into DC power supply signals $V_1$-$V_6$ for the components in the apparatus. Thus, the user interface receives a power signal $V_1$, the microprocessor 110 receives a power signal $V_3$, the RF line-up 102 receives a power signal $V_3$, the microwave line-up receives a power signal $V_4$, the signal conditioning and general interface circuits 108 receives a power signal $V_5$, and the watchdog 1015 receives a power signal $V_6$.

Figure 2:
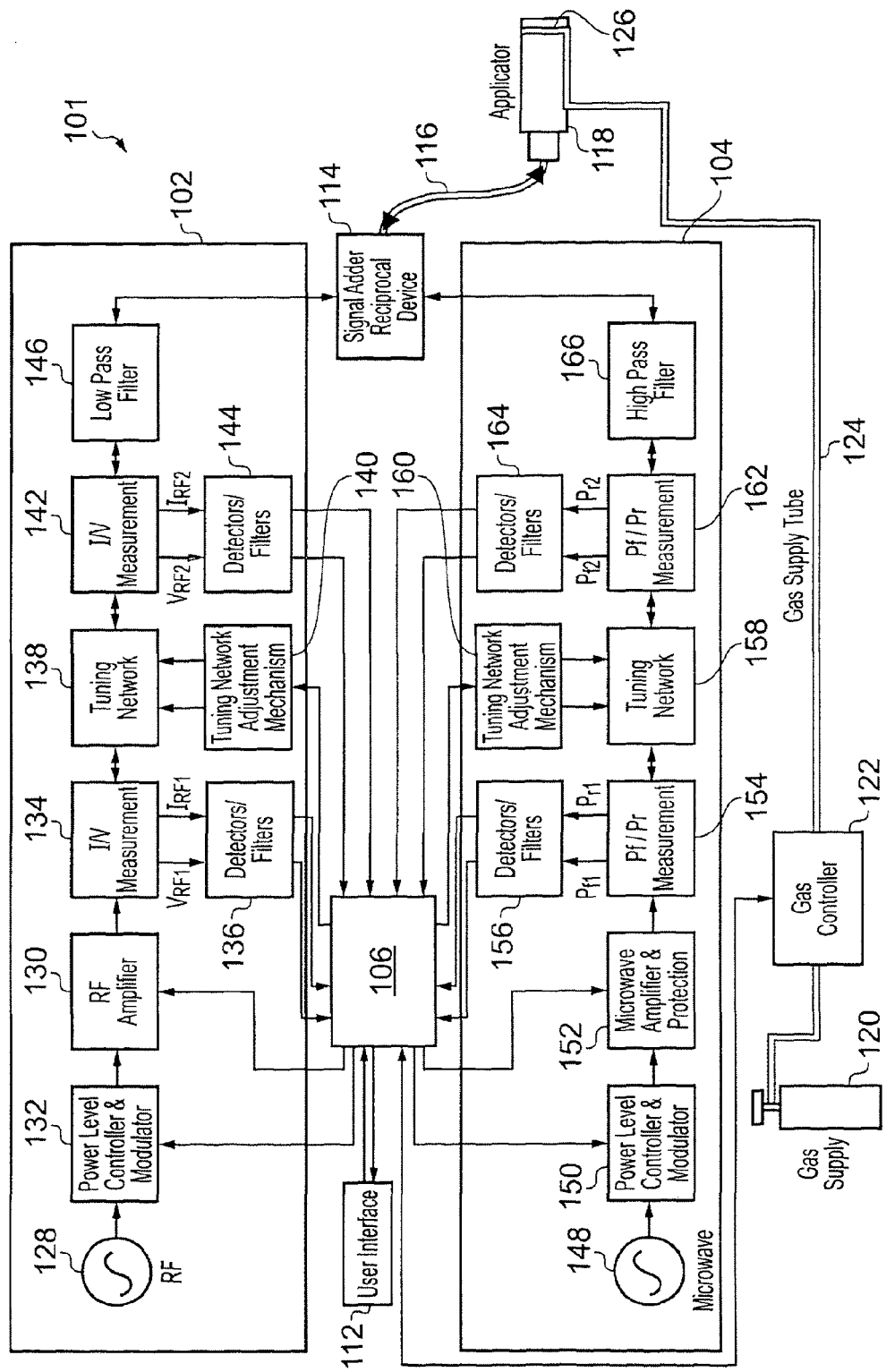
FIG. 2 is a schematic diagram of electrosurgical apparatus according to another embodiment of the invention, including a gas feed, whereby the apparatus is capable of delivering RF energy, microwave energy and thermal/non-thermal plasma into tissue.

FIG. 2 is a system diagram of an electrosurgical system 101 according to another embodiment of the invention. The subcomponents of the RF line-up 102 and microwave line-up 104 are illustrated, and in this embodiment include tuning elements, as explained below. Components in common FIG. 1 are given the same reference numbers and are not described again.

In this embodiment, the system also includes a gas supply 120 (e.g. a canister of compressed air or inert gas, such as argon) which supplies gas to a gas controller 122 (e.g. one or more flow switches and/or valves) that operates under instructions received from the controller 106. The gas controller 122 is connected to permit selective delivery of gas to the probe 118, wherein it may be used in the formation of a non-thermal or a thermal plasma, as described below. The gas supply system used in the present invention may be similar to the gas control system disclosed in WO 2009/060213, which is incorporated herein by reference.

Thus, the probe 118 may take in RF energy, microwave energy and gas and emit RF energy to cut tissue, microwave energy with to coagulate and/or ablate tissue, non-thermal plasma to sterilise tissue, e.g. to kill bacteria resistant inside natural orifices or caused by foreign bodies introduced inside the body, i.e. metallic inserts, and/or thermal plasma to cut tissue or perform surface coagulation, e.g. for the treatment of ulcers on the surface of the tissue.

Microcontroller 110 and signal conditioning and general interface circuits 108 may also be used to provide control signals to gas controller 122 to control the flow rate, gas mixture and gas delivery profile to the probe 118 in accordance with the plasma required to be generated at the probe 118, i.e. the controller 122 may establish the gas delivery conditions depending on whether a non-thermal plasma is wanted (e.g. to provide a local return path or to sterilise tissue) or thermal plasma is wanted (e.g. to cut tissue or perform tissue surface ablation). For sterilisation and for providing the local return, a high voltage state pulse e.g. 400 V peak for 1 ms, may be used to initiate the plasma, followed by a microwave pulse for a duration of 10 ms with a duty cycle of 10% and an amplitude of 30 W. For thermal plasma, the duty cycle may be increased to 60% and the amplitude to 60 W.

The RF line-up 102 comprises an RF signal generator 128 for generating RF EM radiation having a first stable fixed frequency, which in this embodiment is 500 kHz. The RF signal generator may comprise an oscillator, e.g. a Clapp oscillator or the like, which outputs a low voltage (power) RF signal at the first frequency. In an alternative embodiment, a separate oscillator may not be required; the RF signal may be produced directly from a microcontroller in the controller, since known microcontroller devices are capable of outputting analogue signals up to 300 kHz. The output of the signal generator 128 is used as a low power signal for driving an RF amplifier 130, which outputs RF EM radiation at voltage and current levels suitable for tissue cutting. The power output by the RF amplifier 130 is controlled by a power level controller and modulator unit 132, which may comprise an adjustable voltage source and an ON/OFF switch, e.g. variation in the drain voltage of the output stage that uses one or more MOSFET transistors, i.e. one single ended MOSFET, two MOSFETs arranged as a half-bridge or four MOSFETs arranged as a full bridge. If the adjustable voltage source can reduce its voltage to zero rapidly enough, i.e. in around 1 µs, the ON/OFF switch may be omitted. Where the ON/OFF switch is employed, it may take the form of a series connected MOSFET transistor. The output from the oscillator 128 may drive a switching device, e.g. power MOSFET or the like, to apply a pulsed input to the RF amplifier 130.

The output from the RF amplifier 130 is received by a first measurement unit 134, which is arranged to measure the current and voltage of the RF EM radiation output produced by the RF amplifier 130. The first measurement unit 134 may extract (e.g. couple or sample) signals $I_{RF1}$, $V_{RF1}$ corresponding to (e.g. proportional to) the measured current and voltage respectively. The output signals $I_{RF1}$, $V_{RF1}$ are received by first detection unit 136, which may be arranged to process and/or condition the output signals $I_{RF1}$, $V_{RF1}$ to extract information indicative of there relative magnitude and, optionally, phase. This information is input to the controller 106 for use in controlling the operation of the system 100.

The output from the first measurement unit 134 is input to an RF tuner 138, which has an adjustable reactance present on the RF line-up 102 for matching the impedance of the apparatus with a load (e.g. biological tissue) present at the distal end of the probe 118. The adjustable reactance of the RF tuner is effected by a tuning network adjustment mechanism 140 (e.g. an array of switches, a linear or stepper motor, a PZT device or a magnetostrictive (e.g. Terfenol D-based) actuator or the like) that is under the control of the controller 106. The RF tuner 138 may have both an adjustable inductance and an adjustable capacitance, which may be independently controlled by the controller 106. A detailed example of this arrangement is discussed below with reference to FIG. 4.

The output from the RF tuner 138 is received by a second measurement unit 142, which is arranged to measure the current and voltage of the RF EM radiation output produced by the RF tuner 138. The second measurement unit 142 may extract (e.g. couple or sample) signals $I_{RF2}$, $V_{RF2}$ corresponding to (e.g. proportional to) the measured current and voltage respectively. The output signals $I_{RF2}$, $V_{RF2}$ are received by second detection unit 144, which may be arranged to process and/or condition the output signals $I_{RF2}$, $V_{RF2}$. The resulting information is input to the controller 106 for use in controlling operation of the apparatus 100.

The first detection unit 136 and second detection unit 144 may each take the form of a zero crossing detector or a maxima/minima detector, which can be configured to detect when the voltage and current waveforms are in phase with one another (capacitive reactance is equal in magnitude and opposite in sign to inductive reactance) or to detect peak voltage/current values, i.e. a voltage maxima and a current minima is indicative of a high impedance load. The zero crossing detector and the maxima/minima detectors can be realised using analogue components, i.e. operational amplifiers, or can be realised in software. Circuits that produce these functions based on operational amplifiers are know to a person experienced in the art of analogue circuit design.

A voltage/current detector may be used before and after the RF tuner 138 in order to quantify the power level at the input to the tuner and at the output from the tuner to ensure that power is not lost in the tuning network itself, i.e. due to non ideal (lossy) inductors and capacitors within the tuning network. The voltage and current measurements may be detected at the output only since when all of the source energy is delivered into the tissue load, no reflected voltage/current will be detected on the input side of the tuner.

In the instance where the RF amplifier 130 comprises of two transistors connected in a half bridge configuration or four transistors connected in a full bridge configuration, it may be desirable to measure the voltage across and the current flowing through the transistors, i.e. before the tuning network, and use this information to control the switching of the transistors to ensure optimal operation, i.e. to achieve zero voltage or zero current crossing i.e. where the power dissipation in the device is theoretically zero. In this arrangement, the controller 106 may be used to decide when to turn on or turn off the power transistors in the RF amplifier 130 based on the detected voltage and current information.

For the RF stage, the impedance is found by dividing the voltage by the current and measuring the phase difference between the two so that the complex impedance can be extracted. Alternatively, the phase information alone may be used to control the system, i.e. adjust the value of 'C' or 'L' when a phase lead/lag is detected. A high value of voltage and a low value of current indicates a high impedance value and conversely a low value of voltage and a high value of current is indicative of the low value of impedance.

In a practical implementation, the values of voltage, current and/or phase angle between the two would first be measured and then an adjustment would be made to either the value of capacitance (C) or inductance (L) within the RF tuner 138 to establish a change in magnitude of the voltage/current and the phase. If the phase angle is increased, then the same element may be adjusted back to the original position (value of L or C) and then moved in the opposite direction (higher or lower L or C) or it may be preferable to move back to the start position and then vary the value of the other component (L or C) in the network. This tuning process is iterative.

Alternatively, look up tables may be used, whereby physical adjustments are made to the values of L or C or both L and C based on the measured values of voltage, current and/or phase angle. The control signals to electromechanical actuators, semiconductor switches, DC biases on magnetic materials, etc will vary the values of L and/or C in the tuning network and these signals are provided by controller 106.

For series or parallel resonance circuits, the voltage and current is in phase, i.e. the phase angle between the two is zero, and the magnitude of the capacitive reactance of the system (including the delivery cable 116, the applicator 118 and the tissue) is the same as the magnitude of the inductive reactance (which will include the delivery cable 116 and the applicator 118) and the two are 90° out of phase. Thus, when the phase angle is zero the resonance condition is achieved and the maximum value of voltage or current that is achievable by the circuit components in the particular configuration used (taking into account magnetic, dielectric and resistive losses within the network) will be delivered into the tissue. The circuit used to detect the difference in phase between the voltage and the current may be a simple exclusive OR (EXOR) gate based phase detector with appropriate voltage/current scaling/limiting applied to clamp the signal amplitude going into the detector, i.e. if this is a TTL device, the amplitude should not exceed 5 V.

The output from the second measurement unit 142 is input to a low pass filter 146, which operates to transmit only RF energy therethrough, therefore ensures that only RF EM radiation is transmitted towards the probe from the RF signal generator and prevents any microwave EM radiation that may be reflected from the probe or transmitted through the signal combiner (e.g. duplexer-diplexer unit) 114 to the RF input port from reaching the components on the RF line-up 102, i.e. causing damage to the output stage.

The microwave line-up 104 includes a microwave frequency source 148 (e.g. microwave signal generator) that is used to generate a low power signal at a second frequency that is higher than (e.g. at least one order of magnitude higher than, preferably two, three or more orders of magnitude higher than) the first frequency (e.g. 5.8 GHz). The frequency source 148 may be a voltage controlled oscillator (VCO), dielectric resonator oscillators (DRO), Gunn diode oscillator or the like. The output of the frequency source 148 is received by a power level controller and modulator unit 150. The power level controller and modulator unit 150 may include a modulation switch arranged to enable the microwave channel to be operated in a pulsed mode, and a power control attenuator arranged to enable the user to control the level of power delivered into the tissue.

The output of the power level controller and modulator unit 150 is received by an amplifier and protection unit 152 arranged to amplify the power of the low power signal to a level suitable for sealing or coagulating or ablating biological tissue. The amplifier and protection unit 152 may include a driver amplifier to amplify the output signal level produced by the frequency source, and a power amplifier to amplify the signal produced by the driver amplifier to a level suitable to cause tissue sealing or coagulation or ablation. To protect the amplifiers and source from high levels of reflected microwave energy, the output from the power amplifier may be connected to a microwave circulator. The circulator only allows microwave power to flow in a clockwise direction, hence any reflected power coming back into power amplifier will be absorbed by power dump load if the circulator is a three port device, where the first port takes in the output power from the amplifier. The second port outputs this power into a cable assembly and probe and receives power back from the probe and cable assembly when the probe is mismatched with the impedance of the tissue. The third port is connected to a power load that is capable of absorbing the reflected power and is very well matched with the impedance of the circulator. The impedance of the matched load is preferable the same as the impedance of the system, i.e. $50+j0\Omega$. A directional coupler may be connected between the third port of the circulator and the input to the matched load to enable the reflected power to be sampled.

The output of the amplifier and protection unit 152 is input to a first power coupling unit 154, which may comprise a forward directional coupler and reflected directional coupler arranged to sample the forward and reflected microwave energy on the microwave channel. The sampled forward and reflected power levels are input respectively to a forward and reflected first power detection unit 156, in which the power levels are detected, e.g. using diode detectors or heterodyne/homodyne detectors, to sample a portion of the forward and reflected power and enable magnitude or magnitude and phase or phase only information to be extracted from the sampled signal. The signals produced by the first power detection unit 156 are input to the controller 106 to enable levels and/or phase of forward and reflected power to be used to calculate the net power delivered into the tissue and to determine the necessary input signals going into the power level controller and modulator 150 to ensure that the actual delivered power or energy is equal to the demanded power or energy.

This embodiment uses a dynamic impedance matching system to enable the microwave energy developed by the amplifier and protection unit 152 to be matched, in terms of impedance, with the load presented to the distal end of the probe 118 which represents the state of the biological tissue. This invention is not limited to the use of an automatic tuning mechanism for the microwave power delivery system, i.e. the distal end of the probe (the radiator) may be matched to one particular biological tissue type/state at the frequency of operation or the impedance of the probe may be mechanically adjusted, i.e. by a mechanism included in the hand-piece to provide a level of matching between the probe impedance and the impedance of the tissue in contact with the probe. The output of the first power coupling unit 154 is received by a tuning network 158, which has an adjustable impedance on the microwave line-up 104 that is determined by the state of a tuning network adjustment mechanism 160 under the control of controller 106, based on information gathered from first power detection unit 156 and a second power detection unit 164.

The output of the tuning network 158 is input to a second power coupling unit 162, which may be configured in a similar manner to the first power coupling unit 154 to sample forward and reflected power levels from the microwave line-up 104 and input them respectively to a second forward and reflected power detection unit 164, which forwards the detected power levels and/or phase information to the controller 106.

The information made available by the first and second power detection units, 156, 164 may be compared to determine the adjustments required to the tuning network 158 to enable the power source to be impedance matched to the tissue load.

The output from the second power coupling unit 162 is input to a high pass filter 166, which operates to transmit only microwave energy therethrough, therefore ensures that only microwave EM radiation is transmitted towards the probe from the microwave signal generator and prevent any RF EM radiation that may be reflected from the probe from reaching the components on the microwave line-up 104. The high pass filter may be a reciprocal device, enabling it to pass signals in both directions.

More detailed examples of the microwave channel are discussed below with reference to FIGS. 7 to 9.

In use, the controller 106 operates to control the values of capacitance and inductance of the tuning elements of the RF tuner 138 during the supply of RF energy and the distributed tuning elements of the tuning network 158 during the supply of microwave energy to match the impedance of the respective channels to the load at the distal end of the probe 118. In practice, the tuning elements may be variable capacitances/inductances (lumped elements) and variable stubs/microstrip transmission lines or power PIN/Varactor diodes (distributed elements) respectively. The RF energy and microwave energy may be transmitted simultaneously, so simultaneous matching may be performed by the controller 106. The low pass and high pass filter ensure that the returned signals used for tuning contain energy only at the frequency of the particular source. Impedance matching in this context refers to maximising the transfer of energy into tissue (through conduction of RF energy and radiation of microwave energy) by complex conjugate matching of the source (i.e. the apparatus) to the tissue load. It may be noted that the microwave source can deliver energy by radiation and conduction, but the return path is localised for the microwave currents. RF and microwave energy may be required to be delivered simultaneously when the microwave energy is used to create a plasma to set up a preferential return path for the RF currents to flow. In this instance, the RF energy may be used to cut tissue. It may also be desirable to deliver RF and microwave energy simultaneously into the tissue to achieve enhanced tissue effects, i.e. the RF energy may be modulated with the microwave energy to cause simultaneous coagulation and cutting or the microwave field to assist with cutting through fatty tissue or to take over cutting when tissue becomes charred.

It may be preferable for oscillators 128 and 148 to be phase locked to a stable temperature compensated crystal reference source in order for energy at RF and microwave frequency to be at a fixed frequency. In the case of RF oscillator 128, the signal may be produced by microcontroller 106, which will be referenced to a stable source oscillator for timing, i.e. a temperature compensated crystal oscillator or the like.

The gas controller 122 operates to control the flow of gas into gas supply tube 124, which connects the gas supply 120 to the probe 118. At the distal end of the probe, the gas supply tube 124 has an outlet arrangement 126 for creating a line of gas flow in the region of the distal end of the probe 118. The position of the line of gas flow is arranged to coincide with a high voltage electric field set up using the RF energy or the microwave energy or a combination of both. The high voltage electric field, which may only be present for a short duration, e.g. a pulse of 10 ms or less, may act to strike plasma from the line of gas flow. Once struck, the plasma may be maintained by the microwave EM radiation from the apparatus, e.g. by matching the impedance of the microwave line-up 104 to the plasma and thereby efficiently coupling the microwave energy. The matching may be achieved dynamically, e.g. using an impedance adjustor in the microwave line-up 104 or may be prearranged, e.g. by making the impedance of applicator 118 well matched to the impedance of the microwave line-up 104 when conducting gas or plasma is present therein. The high voltage strike may be produced using a lower frequency energy source, i.e. the RF source running at 500 kHz.

The electric field produced by the microwave power generator may be sufficient to strike and maintain plasma and so the RF source or microwave impedance adjuster may not be required to create and sustain the plasma necessary to produce the preferential return path for the RF current. For example, 80 W of microwave power at 5.8 GHz may be used to strike plasma and 20 W of power at 5.8 GHz may be used to sustain the plasma once it has been struck. The small geometries associated with the probes used in this application implies that high E-fields are present, i.e. the spacing between the two electrodes may be less than 1.5 mm. In this instance, the RF energy may be used to cut tissue and the impedance adjuster may be used to ensure that the microwave energy in contact with tissue is well matched to the impedance of the tissue to ensure maximum energy transfer is achieved and that the energy delivered from the radiating section of the applicator can be well quantified, i.e. taking into account the insertion loss of the delivery cable and the applicator, a user demand of 10 W for 10 seconds to deliver 100 J of energy into the target tissue can be achieved with a high degree of confidence even when the impedance of the tissue changes during the coagulation or ablation process.

In one embodiment, the probe 118 may comprise a planar bipolar antenna structure or parallel plate transmission line comprising two conductive layers that are spatially separated from one another in a direction normal to the plane of the structure. In use, the conductive layers are parallel to one another. The conductive layers comprise a first (active) electrode that is connected to the inner conductor of a coaxial feed line 116, and a second (return) electrode that is connected to the outer conductor of the coaxial feed line 116. An edge of each electrode is exposed at the distal end of the probe, thereby forming, in use, a pair of parallel conducting lines separated from one another. The separation may be small, e.g. 2 mm or less. In one particular embodiment of a parallel plate transmission line, the width of the active plate is 2.0 mm, the length of the active plate is 12.7 mm, the width of the return plate is 2.2 mm, the length of the return plate is 13.2 mm, and the thickness of the substrate material that separates the two plates is 0.6 mm. In another embodiment, the width may be 1.3 mm, the length 5 mm and the spacing between the two plates may be 0.3 mm. The substrate material is Z-cut quartz, with a relative permittivity of 4.0 and the plates are each produced by depositing a layer of copper, followed by a layer of gold. The thickness of layers of metallization is between 3 μm and 5 μm. The layer of gold protects the copper from oxidising and is also a material that can be used within the body. The plates may also be single layers of gold or silver only.

The dielectric material separating the two electrodes may also be exposed at the distal end of the probe 118. The outlet arrangement 126 may comprise a very small pipe located at one end of the exposed electrode edges. The pipe may be integrated into the probe 118, e.g. be contained in the dielectric material.

In another embodiment, the electrodes may extend beyond the dielectric material to define a cavity at the distal end of the probe. The cavity may be closed, e.g. separated from the tissue load, by a cap (e.g. a quartz window) mounted between the distal edges of the electrodes. The plasma may be formed in the cavity, whereby it is partially (in the absence of the cap) or fully (where the cap is present) enclosed inside the antenna structure. This may ensure plasma is sustained in all tissue environments; i.e. it is not affected by wet tissue and thermal and non thermal plasma may be emitted for surface coagulation and orifice sterilisation respectively.

Figure 3:
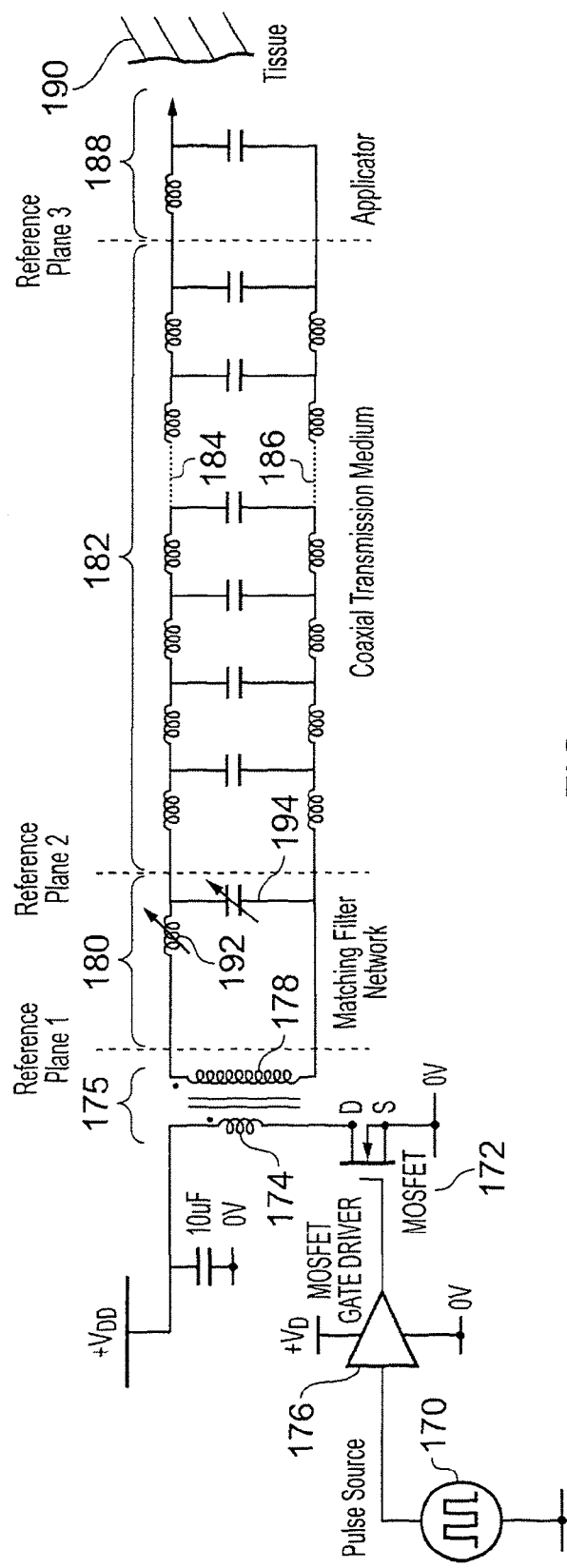
FIG. 3 is a schematic circuit diagram of an RF signal generator on the RF channel used in an embodiment of the invention.

FIG. 3 shows components of an example of an RF channel that can be used in the embodiments discussed above. In this example a pulse source 170 is used as the primary oscillator. The pulse oscillator is arranged to generate a pulsed (e.g. square wave) output having a stable (e.g. fixed) frequency in the range 10 KHz to 100 MHz and a duty cycle of less than 1% to greater than 90%. The pulsed output is used to switch ON/OFF a power MOSFET 172, whose operational status determines whether or not current flows through a primary coil 174 of a transformer 175. The magnitude of the bus or supply voltage $V_{DD}$ may be adjustable (e.g. by the apparatus controller) to control the magnitude of the voltage of the output RF energy or measurement signal. Adjustment of $V_{DD}$ and/or the duty cycle of pulse source 170 may provide a suitable means controlling the level of RF power produced by the generator.

The output of the pulse source 170 may not be sufficient to drive the power MOSFET 172, so a gate driver 176 may be connected to amplify the pulse source output voltage and to provide sufficient current to charge/discharge the input capacitance of the power MOSFET 172 to enable the device to be switched ON and OFF in an efficient manner, i.e. the current, I, available from the MOSFET driver and the input capacitance, C, of the device are connected using the following equation: $I=C\, dv_{gs}/dt$, where $dv_{gs}$ is the gate source voltage required to switch the device ON/OFF and dt is the time to turn the device ON/OFF (the rise/fall time+turn on/off delay). The single ended MOSFET arrangement may be replaced by a half bridge arrangement comprising two transistors connected in series or a full bridge arrangement comprising four transistors connected in a 'H' configuration. These configurations are known to an RF engineer with experience in the field of switch mode power supply design.

The secondary coil 178 of the transformer 175 is connected via an RF tuner 180 between the inner conductor 184 and outer conductor 186 of a coaxial transmission medium 182, which is depicted in FIG. 3 using representative reactive components. The lumped element equivalent circuit of this line-up is a series inductance and a shunt (parallel) capacitance. In this example, the RF tuner 180 performs two functions: filtering the pulsed output of the secondary coil 178 to extract a sinusoidal RF signal (the fundamental) for conveying to the probe 188 and providing a reactance that acts to match the impedance of the apparatus with the tissue load 190. For simplicity, the RF tuner 180 in FIG. 3 is shown as comprising a variable inductance 192 in series with the secondary coil 178 and a variable capacitance 194 connected in parallel (shunt) across the output of the generator. This arrangement may be changed to a variable series capacitance followed by a variable shunt inductance. It may be preferable to use one fixed value tuning element (L or C) and one variable tuning element (C or L) rather than two variable tuning elements. It may be preferable to place the shunt tuning element in front of (or preceding) the series tuning element. It may be preferable to use additional tuning elements in the network, i.e. a shunt connected capacitor followed by a series connected inductor followed by a second shunt connected capacitor. The inductor and capacitors may also be interchanged. It may be preferable to replace the tuning network with a single shunt capacitor connected across the output transformer used to adjust the phase angle between the voltage and current to provide power factor correction.

The applicator 188 may be a parallel plate capacitor (or parallel plate transmission line for microwave frequency analysis) comprising two metallic plates (active and return) separated by a layer of dielectric material, e.g. quartz or ceramic, where the metallic layers are each 4 μm of copper followed by 2 μm of gold and the plate dimensions are 2 mm×12 mm.

Figure 4:
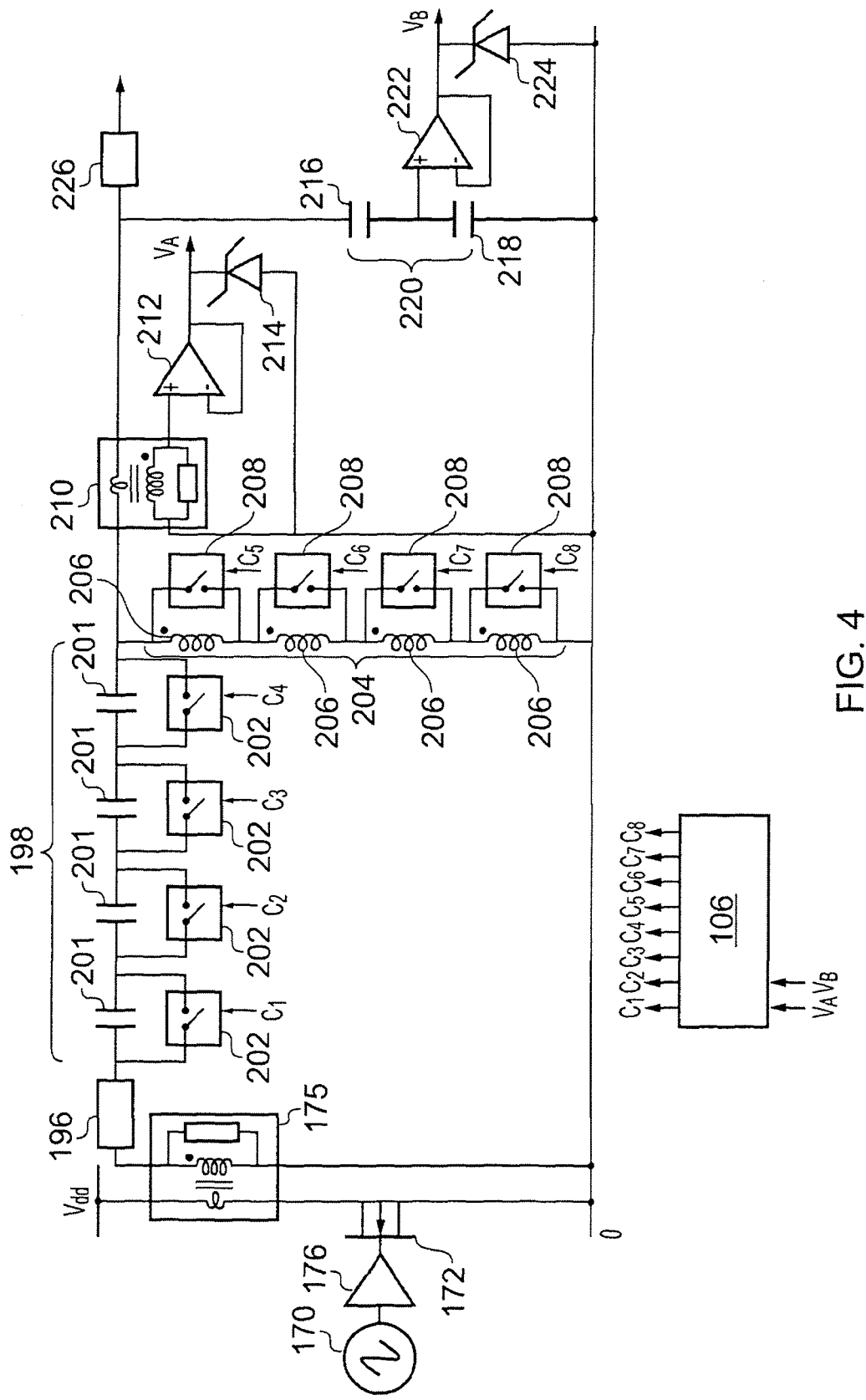
FIG. 4 is a schematic circuit diagram of an RF tuner and an RF signal detector on the RF channel used in an embodiment of the invention.

FIG. 4 shows a more detailed version of the RF channel illustrated in FIG. 3, in which the components that achieve the functions of the RF tuner described above are shown. Components having the same function as in FIG. 3 are given the same reference numbers and are not described again.

In FIG. 4 the secondary coil of the transformer is connected to a low pass filter 196 that extracts the fundamental sinusoidal signal from the pulsed RF output. The output of the low pass filter 196 is input to a variable capacitor 198 connected in series with the secondary coil of the transformer 175. In this example, the variable capacitor 198 comprises a plurality (four in this case) of capacitors 201 that can be independently switched into or out of the channel. Each capacitor 201 has a bypass switch 202 that can be used to switch out the respective capacitor when closed by shorting the plates together. The bypass switches 202 are operated by respective control signals $C_1$-$C_4$ produced by controller 106. The capacitors 201 may have different capacitances, e.g. arranged in a binary sequence of 1×, 2×, 4× and 8× a base capacitance.

Similarly, a variable inductor 204 is connected in parallel (shunt) to the secondary coil of the transformer 175 at the distal end of capacitor chain 201. In this example, the variable inductor 204 comprises a plurality (four in this case) of inductors 206 that can be independently switched into or out of the channel. Each inductor 206 has a bypass switch 208 associated with it to enable the start and finish of any of windings 206 to be shorted together or bypassed. The bypass switches 208 are operated by respective control signals $C_5$-$C_8$ from the controller 106. The inductors 208 may have different inductances, e.g. arranged in a binary sequence of 1×, 2×, 4× and 8× a base inductance in order to provide as large a variation in possible load impedances that the system can be matched with as possible, i.e. cover as much of the Smith chart as possible.

Figure 5:
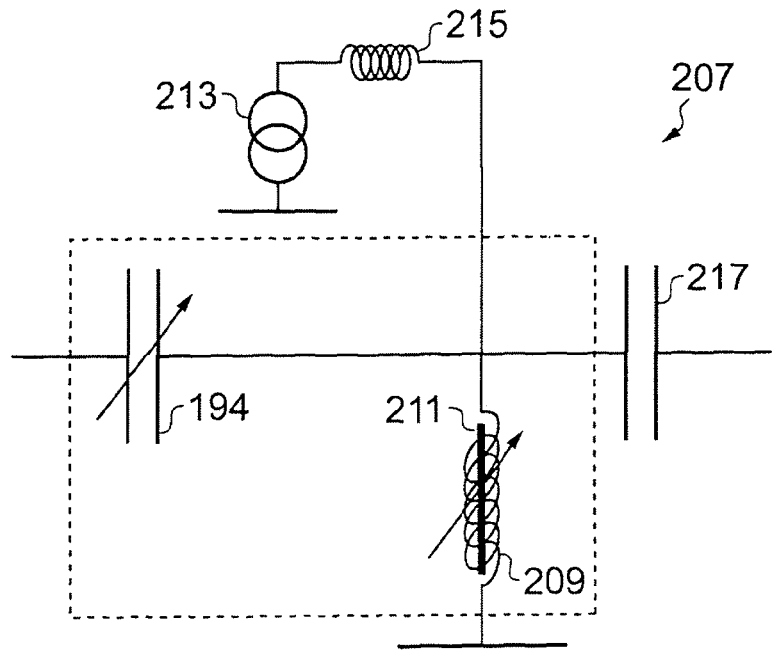
FIG. 5 is a schematic circuit diagram of a means of varying the inductance of a variable element tuner used in an embodiment of the invention.

FIG. 5 shows an alternative implementation of a variable inductor 207. Here, a solenoidal coil of wire 209 is wound around a bar of magnetic material 211 to form the inductor for the tuned circuit. The variable inductor 207 operates mechanically by varying the distance the bar 211 is inserted within the coil 209. The magnetic material of the bar has a high relative permeability (flux multiplier) to enable a small movement of the bar 211 to produce a notable change in the inductance of the coil 209. The bar 211 may be moved backwards and forwards along its axis under the control of a pair of solenoids or a single solenoid and a control circuit that enables current to be driven on both directions along the winding. Alternatively, a magnetostrictive or piezoelectric (PZT) material based actuator may be used to move the rod.

In FIG. 5, a bias current (I) is applied to the bar from a DC (or low frequency) current source 213. The current sets up a magnetizing force (H), where H=number of turns (N)×current (I) divided by the length of the solenoid or winding (l)), which acts to change the value of relative permeability or magnetisation to produce a change in inductance (L). This arrangement assumes that magnetisation (M) is proportional to relative permeability, which is a function of H, and that the magnetisation curve is non-linear, i.e. 'S' shaped, thus L=f(H) or L=f(I).

In FIG. 5, an inductor 215 is used to block the higher frequency RF signal from entering current source 213. The inductance of blocking inductor 215 is much greater than that of tuning inductor 211, which produces high enough inductive reactance to block the RF signal. A DC blocking capacitor 217 is connected in series with the output of the tuning circuit to ensure that DC current produced by current source 213 cannot flow along cable assembly, through applicator and into the patient. The magnetic material 209 placed inside tuning coil 211 should be low loss at the frequency of operation, i.e. iron dust or ferrite may be used, and may exhibit a non linear magnetisation response to applied field in order to enable the inductance to be adjusted using this arrangement. The DC or low frequency bias field will set the operating point for the RF signal.

Figure 6:
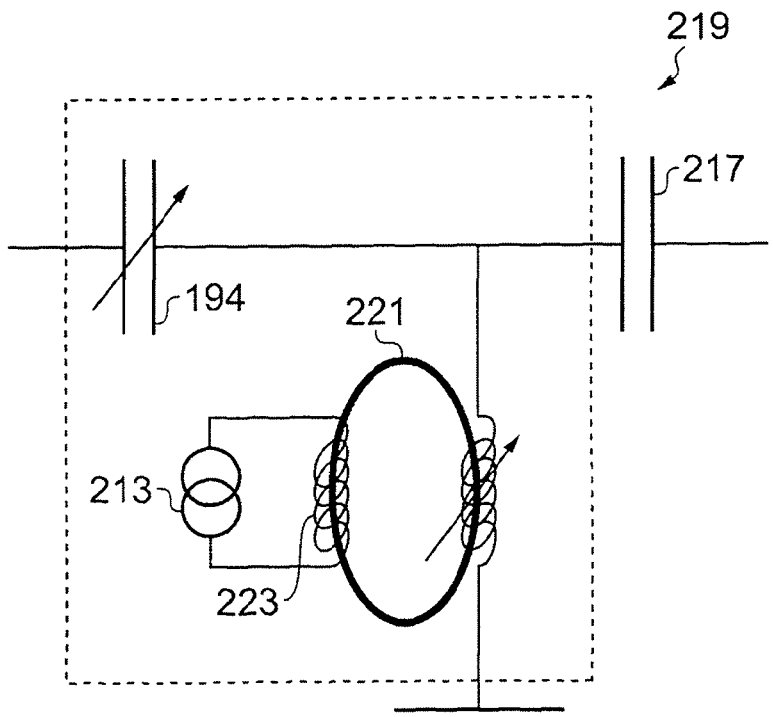
FIG. 6 is a schematic circuit diagram of another means of varying the inductance of a variable element tuner used in an embodiment of the invention.

FIG. 6 shows a further embodiment of a variable inductor 219 that may be used in the RF tuning circuit. This arrangement resembles FIG. 5 except that the rod 209 of magnetic material is replaced by a toroidal core 221, and a separate inductive winding 223 is used to apply the DC or low frequency AC field to the material to change the magnetisation or the operating point to produce a variation in the value of tuning inductance, used to tune the circuit or to perform the matching function.

Returning to FIG. 4, the position of the variable capacitor 198 and variable inductor 204 may be reversed. The invention may also work with a mixture of inductors and capacitors connected both in parallel and in series with the secondary coil of the transformer, as long as the series reactance and parallel reactance are independently adjustable.

In some embodiments it may be desirable to further amplify the RF signal output from the secondary coil of the transformer. One or more additional transformer circuits may be provided for this. Alternatively or additionally, a power amplifier, e.g. a push-pull amplifier, half bridge, full bridge or the like, may be provided between the secondary coil and the adjustable reactance (variable inductance or capacitance).

FIG. 4 also shows schematically one example of how the voltage and current of the RF signal can be measured. A detection transformer (or current transformer) 210 may have a primary coil connected in series with the secondary coil of the transformer 175 (i.e. on the RF channel itself). Current transformer 210 may also be connected on the primary side of transfer 175. A secondary coil of the detecting transformer may be connected to ground such that current in the primary coil (on the RF channel) excites a signal in the secondary coil. This is known as a current transformer (CT), where the primary winding is normally a single turn in order to minimise the effect the CT has on the performance of the main circuit, i.e. it will only introduce a small inductance, which could be resonated out using a suitable value of capacitance connected across it (if necessary). A burden resistor is also normally connected across the secondary winding of the CT so that a voltage level proportional to the current flowing in the circuit can be extracted. The voltage $V_A$ of the excited signal (which is proportional to the current in the primary coil of current transformer 210) is communicated to the controller 106 following conditioning (in this case using a buffer amplifier 212 and voltage limiting Zener diode 214). The voltage may be measured using a reactive potential divider 220 (implemented using capacitors 216, 218 in this example) connected in parallel to the secondary coil of the transformer 175. The voltage $V_B$ coupled from the potential divider is communicated to the controller 106 following conditioning (in this case using a buffer 222 and voltage limiting Zener diode 224). Further conditioning, e.g. filtering and rectifying, may be applied to each of the voltages $V_A$, $V_B$ before they are input to the controller.

In another embodiment, the potential divider 220 may be incorporated into the parallel adjustable reactance 204, i.e. while the total parallel reactance may be adjustable, one or two fixed elements may be included to provide the measurement signal used to control the system. A further embodiment of potential divider 220 is two resistors connected in series, where the values are chosen to be high, i.e. greater than 10 kΩ, in order to minimise loading on the circuit. The resistors should also be non-inductive at the frequency of operation, e.g. metal film resistors may be the most suitable candidate. In yet another embodiment, the voltage may also be measured by tapping off a winding from the output transformer 175 on the primary and secondary side or by inserting an additional series inductance. This voltage may need to be filtered and clamped prior to being input into the microcontroller or interface board.

A protective low pass filter 226 may be connected between the adjustable reactance and the probe to prevent reflected microwave signals from entering the RF channel, which may otherwise cause damage to the output transistors or result in the circuit bursting into oscillation at a frequency that is different to the desired frequency of operation. The filter may also remove energy present at unwanted frequencies around the RF or microwave range of operating frequencies.

Figure 7:
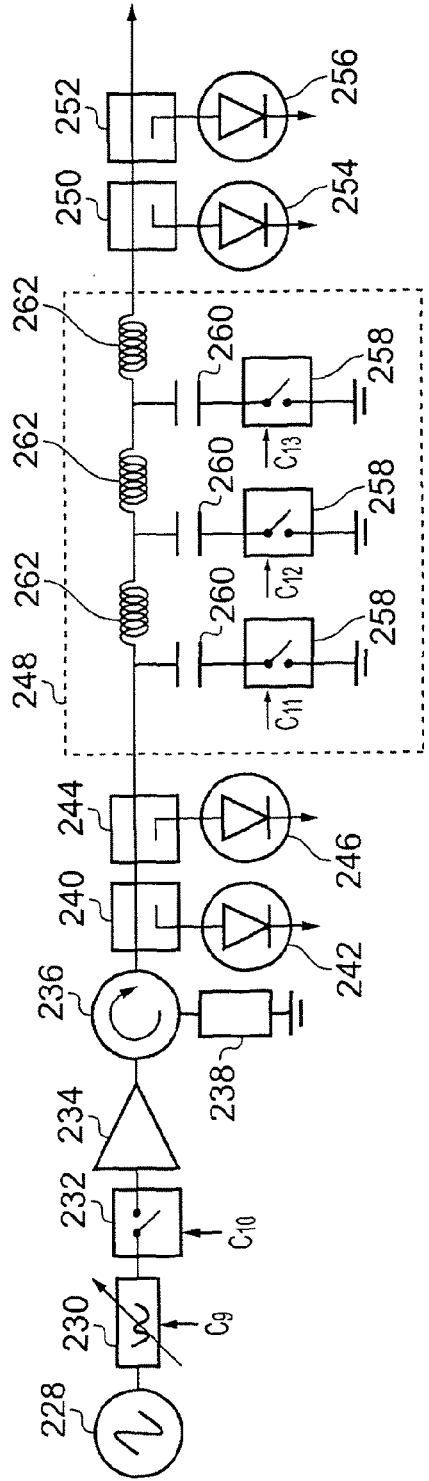
FIG. 7 is a schematic circuit diagram of an impedance adjuster and a microwave signal detector on the microwave channel used in an embodiment of the invention.
Figure 8:
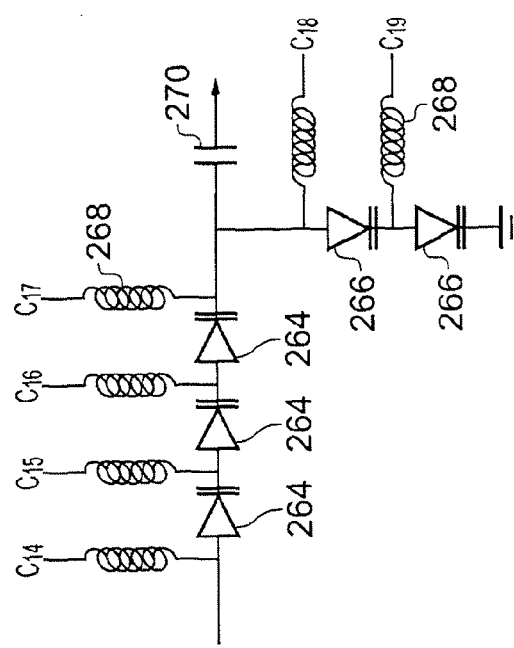
FIG. 8 is a schematic circuit diagram of another example of an impedance adjuster suitable for use in an embodiment of the invention.

FIG. 7 shows a schematic drawing of the components of the microwave channel. The microwave source 228 outputs a microwave signal having a stable (e.g. fixed) frequency. The output from the microwave source 228 is input to a variable attenuator 230, which controls the magnitude of the output based on a control signal $C_9$ from the controller (not shown). The output from the variable attenuator 230 is input to a switch unit 232, which modulates the output based on a control signal $C_{10}$ from the controller. In practice, units 230 and 232 could be combined into one single unit by using a variable attenuator with a response time (time to change the signal attenuation when in receipt of the new digital input signals) that is fast enough to allow the device to act as a modulator or to allow the system to operate in pulsed mode, i.e. if the response time of the attenuator is 100 ns and the system is to be operated in pulsed mode, where the width of the pulse is required to be 5 ms and the off time between pulses is 20 ms, then this device can quite easily be used to serve two purposes. The output of the switch unit 232 is received by a power amplifier 234, which amplifies the microwave signal to a power level suitable to produce a useful therapeutic effect. The output from the power amplifier 234 is input to the first port of a circulator 236. The circulator 236 isolates the amplifier from reflected signals travelling back from the probe. Any reflected signal received back at the second port of the circulator is directed out of the third port into a power dump load 238.

The forward signal from the amplifier is output from the second port of the circulator, which is connected to a forward directional coupler 240, which couples a portion of the forward directed signal into a detector 242. The output of the detector 242 is connected to the controller. The output of the forward directional coupler 240 is input to a reverse directional coupler 244, which couples a portion of any reflected signal into a detector 246. The output of the detector 246 is connected to the controller. The output of the reverse directional coupler 244 is input to a microwave tuning network 248 that has an adjustable impedance. The output of the tuning network 248 is input to a forward directional coupler 250 and reverse directional coupler 252 for coupling a portion of the forward and reflected signal respectively into detectors 254, 256 in a manner similar to the forward and reverse directional couplers 240, 244. The outputs of the detectors 254, 256 are connected to the controller. This invention is not limited to the use of diode detectors, i.e. log magnitude detectors, homodyne phase and magnitude detectors, heterodyne phase and magnitude detectors or Exclusive OR gate (ExOR) phase detectors may be used to implement 242, 246, 254 and 256. The ability to extract phase information as well as magnitude information is beneficial in terms of being able to make accurate adjustments of the RF and microwave tuning networks, provide a greater degree of control and improve the performance of the matching system in terms of accessible impedances that can be matched to, but the invention is not limited by the need to extract phase as well as magnitude information to control the system. The measurement information on the RF and/or microwave channel may be made by measuring phase information only.

The controller may use the outputs from the diode detectors (or other types of detectors) 242, 246, 254, 256 to determine the amount of power delivered to the load (e.g. tissue or gas plasma) and/or as a means for controlling the impedance of the tuning network 248 to minimise the reflected power and match the energy produced by the generator into the changing impedance of the tissue load to provide optimal efficiency of energy delivery into tissue and optimal system performance in terms of minimisation of component heating due to energy being returned to the generator and accurate quantification of energy delivery into target tissue.

The tuning network 248 in FIG. 7 comprises three PIN diode switches 258 connected in shunt to the microwave channel. Each PIN diode switch 258 has an independent DC or relatively low frequency, i.e. up to 10 kHz, voltage control signal $C_{11}$-$C_{13}$ (produced by the controller) for controlling its status. The PIN diode switches operate to switch a respective shunt capacitance 260 (which may be formed by a section of transmission line, i.e. microstrip or co-axial) into the microwave channel. Series inductors 262 (which may also be a section of transmission line) are shown connected between the shunt elements. The combination of shunt capacitance and series inductance form a tuning network or filter and the ability to switch individual elements that form the overall value of capacitance or inductance in and out allows the network to act as a variable tuning filter. In order to increase the tuning range, the number of elements in the network may be increased. The fixed values of shunt capacitance that make up the overall value of tuning capacitance may be weighted, i.e. binary weighted, to provide as large as possible range of variation. The position of the inductors and capacitors that form the tuning network may be interchanged, i.e. the inductors may be connected in shunt and the capacitors in series. Values of capacitance and inductance used in the network may be realised by inserting transmission lines of varied length between the shunt elements and/or between the transmission lines and the switches connected in shunt across the tuning element, i.e. a length of transmission line of physical length equal to one eighth of the guided wavelength will produce an inductive reactance of value equal to the characteristic impedance of the transmission line.

The tuning network 248 may be implemented in other ways. FIG. 8 shows an alternative arrangement in which a plurality of first varactor diodes (or power PIN diodes) 264 are connected in series on the microwave channel and a plurality of second varactor diodes (or power PIN diodes) 266 are connected in parallel to the microwave channel. Controllable DC bias signals $C_{14}$-$C_{19}$ can be applied to control the voltage across each varactor diode 264, 266 to modify the length of the depletion region, which in turn varies the capacitance. Blocking inductors 268 prevent microwave energy from going back into the DC source. These inductors may be realised in microstrip, i.e. a printed inductor or small coils of wire. In this manner the series varactor diodes act as a part of a transmission line having an electrical length that can be varied by up to $$\frac{\lambda}{2},$$

where $\lambda$ is the wavelength of the microwave energy. The parallel shunt varactor diodes may act as a stub having an electrical length that can be varied by up to $$\frac{\lambda}{4}.$$

A DC blocking capacitor 270 is connected between the tuning network and the probe to prevent DC or low frequency AC currents from being delivered into the patient, i.e. it provides a DC patient isolation barrier.

Figure 9:
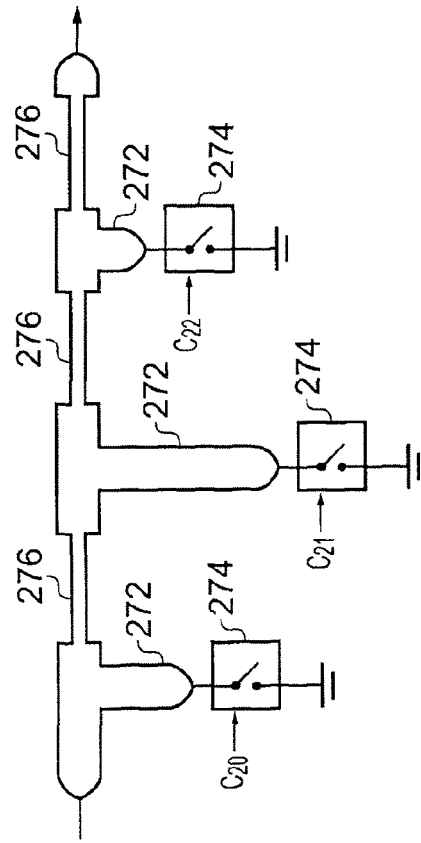
FIG. 9 is a schematic circuit diagram of yet another example of an impedance adjuster suitable for use in an embodiment of the invention.

FIG. 9 shows another alternative arrangement for the tuning network, implemented using microstrip stubs. In this example, three microstrip stubs 272 having differing lengths are connected to a microstrip line on the microwave channel. Each stub 272 can be independently switched between short circuit (switch contact or junction closed) and open circuit (switch or channel open) using PIN diode (or electromechanical) switches 274 under the control of DC signals $C_{20}$-$C_{22}$. The transmission line that forms the stub 272 can be set to a length that represents a range of reactances (capacitive or inductive) or impedances. The arrangement shown in FIG. 9 enables eight different tuning positions, i.e. $2^3$, to be selected. As in the FIG. 7 example, inductors 276 are shown connected in series between the shunt stubs. These inductors are shown here as thin transmission lines realised in microstrip line by printing lines onto a dielectric material that are narrower than the lines that form the characteristic impedance of the transmission line. Other transmission line configurations, where the width/diameter and/or length of the line enables inductors of required inductance at the frequency of operation to be realised, may also be used. This configuration is not limited to using inductors 276, i.e. the width of the microstrip line may be increased to be greater than that required to form a line with impedance equal to the characteristic impedance of the transmission line in order to produce a tuning capacitance rather than a tuning inductance.

In another example, transmission line stubs or waveguide (rectangular or cylindrical) sections that form the stubs may be used instead of microstrip stubs and co-axial trombone structures may be implemented to vary phase.

Figure 10:
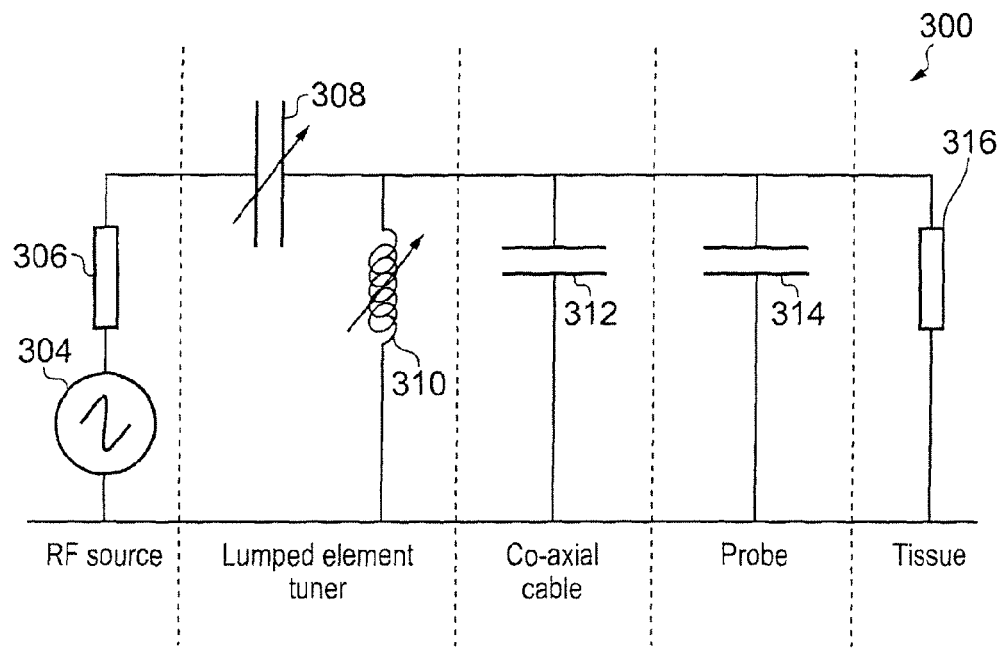
FIG. 10 is a schematic diagram of the complete RF energy delivery channel treated as a lumped element circuit.
Figure 11:
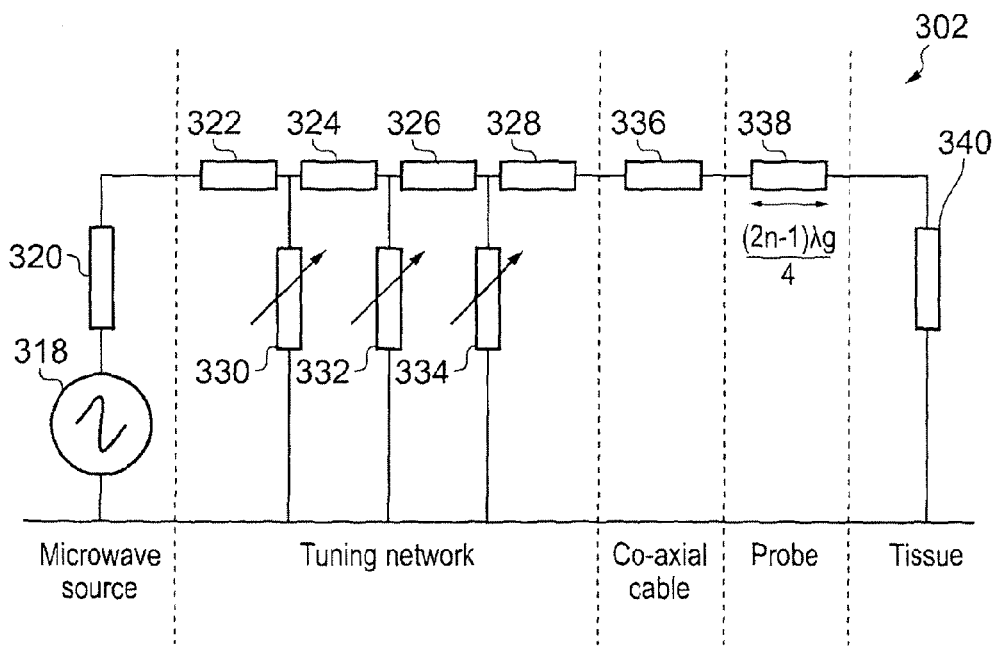
FIG. 11 is a schematic diagram of the complete microwave energy delivery channel treated as a distributed element circuit.

FIGS. 10 and 11 respectively show a lumped element circuit 300 for the RF channel and a distributed circuit 302 for the microwave channel that may be used to analyse the operation of the electrosurgical apparatus.

FIG. 10 shows an RF generator 304 with source impedance 306 connected to a lumped element tuning circuit comprising a variable series capacitor 308 followed by a variable shunt connected inductor 310. A transmission line (i.e. coaxial cable assembly) is represented by shunt capacitor 312 and the probe is represented as a further shunt capacitor 314. The tissue load is shown as shunt resistance 316. If the co-axial cable assembly is a Sucoform 86, which is a 2.2 mm diameter semi-rigid cable assembly from Huber & Huhner, then the capacitance per meter is 95 pF, hence if co-axial cable assembly is 2 m long, then its capacitance is 190 pF. At the RF frequencies of interest for implementing this invention, the probe can be treated as a parallel plate capacitor. If the parallel plate transmission line applicator with the configuration described in brief above is used, where the distance of separation is 0.6 mm, the width is 2 mm, the length is 12.7 mm and quartz with a relative permittivity of 4.1 is sandwiched between the two plates, then its capacitance is 1.53 pF. A representative tissue impedance that may be used in the model for RF cutting is a resistance of between 1 kΩ and 100 kΩ, therefore in the lumped element RF tuning system shown in FIG. 10, the variable tuning network must match the source impedance with a capacitance of value 191.53 pF in parallel with a variable resistance value of between 1 kΩ and 100 kΩ.

The analysis of the microwave channel shown in FIG. 11 is based on a distributed network of impedances, where each element is represented as a complex impedance. Microwave generator 318 is shown connected in series to the impedance of the generator 320 and is nominally 50Ω. The source impedance is connected to a distributed element microwave tuner comprising of four series connected fixed impedances 322, 324, 326, 328 and three shunt connected variable impedances 330, 332, 334 connected between the distal and proximal ends of the aforementioned series impedances. The output of the tuning network is connected to the co-axial cable assembly, which has a nominal impedance 336 of 50Ω. The distal end of the co-axial cable assembly is connected to the probe, which is modelled as a parallel plate transmission line, whose impedance 338 is given by the following expression:

$$Z_{probe} = \sqrt{\frac{\mu}{\varepsilon}}\left(\frac{h}{w}\right) = 377\sqrt{\frac{1}{\varepsilon_r}}\left(\frac{h}{w}\right),$$

where h is the thickness of the dielectric material, w is the width of the parallel plates and $\varepsilon_r$ is the relative permittivity of the dielectric material. In a particular embodiment used to implement the current invention, w=2 mm, h=0.6 mm and $\varepsilon_r$=4.2, which gives an applicator impedance $Z_{probe}$ of 55.19Ω.

The impedance 340 of representative tissue types (in this case, liver and colon) at the microwave frequency of interest may be calculated using values of dielectric constant and conductivity measured or calculated at the frequencies of interest. The dielectric properties at three frequencies of interest are given in Table 1 below:

TABLE 1

Dielectric Properties of representative biological tissue at the microwave frequencies of interest for implementing the current invention

| Tissue | Frequency (GHz) | Conductivity (S/m) | Dielectric constant |
|---|---|---|---|
| Colon | 2.45 | 2.0383 | 53.879 |
| Liver | 2.45 | 1.6864 | 43.035 |
| Colon | 5.8 | 5.5701 | 48.456 |
| Liver | 5.8 | 4.6417 | 38.13 |
| Colon | 14.5 | 18.072 | 35.613 |
| Liver | 14.5 | 14.448 | 27.222 |

To obtain the impedances of the tissues at the microwave frequencies of interest, the bulk value or the TEM plane wave transmission in an infinite medium, may be assumed. For a dielectric material that is absorptive, the expression for calculating impedance is as follows:

$$Z = \sqrt{\frac{-j\omega\mu}{\rho - j\omega\varepsilon}},$$

where Z is the impedance in ohms (Ω), ω is the radian frequency (2πf), where f is frequency in Hertz (Hz), $\mu=\mu_0\mu_r$ is the permeability of free space multiplied by the relative permeability of the magnetic material, $\varepsilon=\varepsilon_0\varepsilon_r$ is the permittivity of free space multiplied by the relative permittivity of the dielectric material, and ρ is the density of the biological material in kg/m³.

Squaring, and then separating the square of the impedance given in the preceding equation into real and imaginary parts gives:

$$Z^2 = \frac{\omega^2\mu_0\varepsilon_0\varepsilon_r}{\rho^2 + \omega^2\varepsilon_0^2\varepsilon_r^2} - j\frac{\omega\rho\mu_0}{\rho^2 + \omega^2\varepsilon_0^2\varepsilon_r^2}.$$

If the modulus is calculated from this expression, and the square root is taken, the magnitude of the impedance can be determined for representative tissue models at the various frequencies of interest. This information is given in Table 2 below:

TABLE 2

Magnitude of impedance for liver and colon at frequencies of interest

| Tissue | Frequency (GHz) | \|Z\| (Ω) |
|---|---|---|
| Colon | 2.45 | 50.38 |
| Colon | 5.8 | 52.53 |
| Colon | 14.5 | 58.08 |

TABLE 2-continued

Magnitude of impedance for liver and colon at frequencies of interest

| Tissue | Frequency (GHz) | \|Z\| (Ω) |
|---|---|---|
| Liver | 2.45 | 56.30 |
| Liver | 5.8 | 59.02 |
| Liver | 14.5 | 65.99 |

The impedance values can be calculated by solving for the real and imaginary parts of Z. These impedances are given in Table 3 below:

TABLE 3

Real and imaginary parts for the impedance of liver and colon at microwave frequencies of interest

| Tissue | Frequency (GHz) | $\Re(Z)$ (Ω) | $\Im(Z)$ (Ω) | \|Z\| (Ω) | Phase angle (°) |
|---|---|---|---|---|---|
| Colon | 2.45 | 49.92 | 6.80 | 50.38 | 7.75 |
| Colon | 5.8 | 51.76 | 8.94 | 52.53 | 9.80 |
| Colon | 14.5 | 55.80 | 16.09 | 58.08 | 16.08 |
| Liver | 2.45 | 55.75 | 7.85 | 56.31 | 8.02 |
| Liver | 5.8 | 58.06 | 10.59 | 59.02 | 10.33 |
| Liver | 14.5 | 63.22 | 18.93 | 65.99 | 16.66 |

The probe may also take the form of a quarter wave transformer by making the electrical length of the probe equal to an odd multiple of a quarter of the loaded wavelength at the frequency of operation. This arrangement may be used to produce a static impedance match between the 50Ω (or other transmission line and energy source of fixed impedance) transmission line 112 and the non-50Ω tissue impedance 451.

From the distributed element microwave tuning system represented by a range of impedance values and variable/fixed line lengths and shown in FIG. 11, the variable elements 330, 332, 334 within the tuning network must match the source impedance 320 to the tissue impedance 340 when the co-axial cable assembly (with impedance 336) and probe (with impedance 338) are connected between the output port of the tuner and the tissue in contact with the probe.

Figure 12:
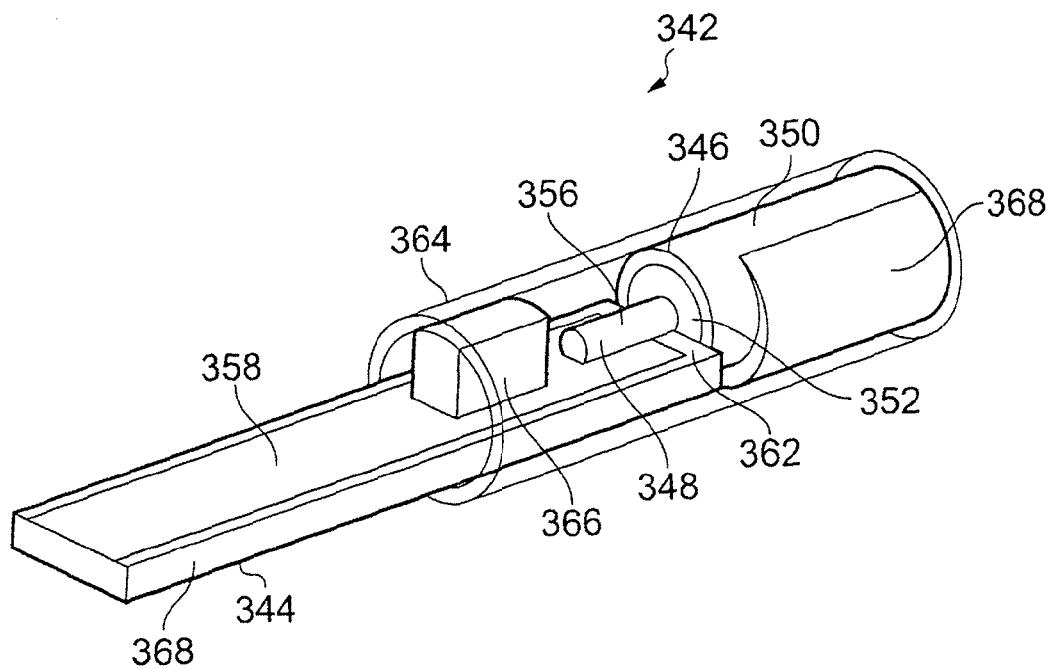
FIG. 12 is a top perspective view of a probe that may be used in an embodiment of the invention.
Figure 13:
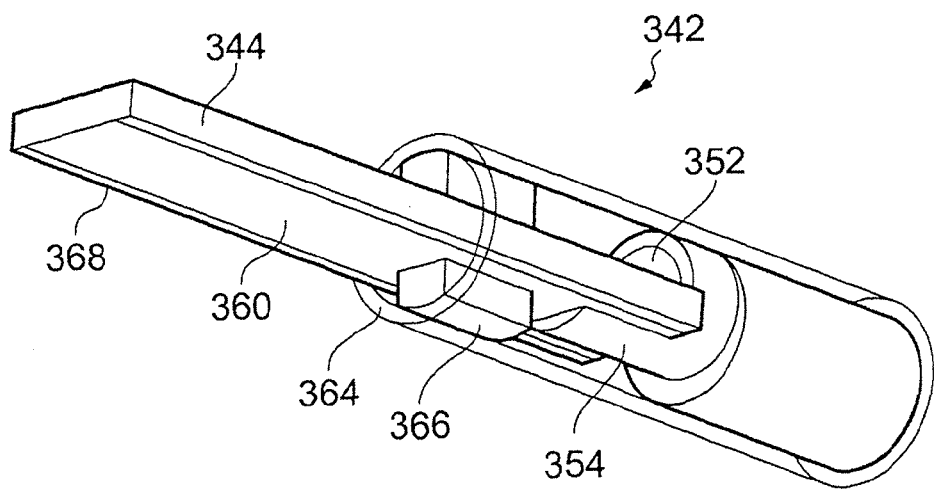
FIG. 13 is a bottom perspective view of the probe shown in FIG. 12.

FIGS. 12 and 13 illustrate views of an example of probe 342 having a bipolar antenna structure that can be used with the invention. The probe 342 has a 0.6 mm thick parallel plate transmission line 344 connected to a coaxial cable 346. The probe is suitable for operation at 2.45 GHz, 5.8 GHz and 14.5 GHz. The coaxial cable 346 comprises an inner conductor 348, an outer conductor 350 and a dielectric material 352 separating the inner and outer conductors 348, 350. At the distal end of the coaxial cable 346, the inner and outer conductors 348, 350 have protruding portions 354, 356 which extend away from the dielectric material 352. The parallel plate transmission line 344 is sandwiched between the protruding portions 354, 356 so that its proximal end abuts the distal end of the coaxial cable. The protruding portion 356 of the inner conductor is arranged to contact an upper conductive layer 358 of the transmission line 344 and the protruding portion 354 of the outer conductor is arranged to contact a lower conductive layer 360 of the transmission line 344.

A gap 362 is provided between the proximal edge of the upper conductive layer and the distal end of the coaxial cable to perform a degree of static impedance matching at the frequencies of interest as well as to prevent shorting between the inner and outer conductors.

A plastic tube support 364 is mounted over the junction between the transmission line 344 and the coaxial cable 346. The inner diameter of the tube support 364 is greater than the outer diameter of the coaxial cable 346 to enable it to be fitted over the cable. The end of the tube that comes in contact with the co-axial cable may be tapered or rounded at the corners to prevent it from damaging the inner wall of the instrument channel of a surgical endoscope (or other surgical device that is used to introduce the device into the body) during the insertion and/or removal process. A mounting structure 368, e.g. glue or the like, is attached between the coaxial cable 346 and the tube support 364 to secure the cable in place. Similarly, mounting blocks 366 (e.g. glue or solid material) are attached between the transmission line 344 and the tube support 364 to secure the transmission line in place and prevent moisture or tissue from getting inside the structure.

In a particular embodiment, the transmission line may comprise a 0.61 mm thick sheet 368 of TRF-41 (dielectric constant 4.1 and loss tangent 0.0035) or a hard quartz material with a similar dielectric constant and loss tangent or a suitable low loss microwave ceramic. The coaxial cable 346 has an outer diameter of about 2.2 mm and a pin diameter of 0.574 mm. The coaxial cable 346 used in the embodiment is UT 85C-LL (from Micro-Coax), but the device is not limited to this particular cable assembly, i.e. Sucoform 86 from Huber & Suhner may also be used to provide similar overall device performance.

The conductive layers 358, 360 on the parallel plate transmission line 344 go right to the distal end of the sheet 368 and are 2.002 mm wide. These conductive layers may be formed by a layer of copper followed by a layer of gold, a layer of gold only or a layer of silver only. The layers of metallization may be deposited directly onto the substrate. In the particular embodiment, the sheet 368 is 2.6 mm wide. This structure is known as a parallel plate transmission line, where the characteristic impedance $Z_o$ is calculated using the equation given above. For a quartz dielectric with a dielectric constant of 4.2, dielectric thickness of 0.6 mm, and width of 2 mm, the characteristic impedance of the structure is 55.19Ω. If the applicator structure was to contain an infinite ground plane, i.e. the width of the top layer of metallization (the active layer) is much narrower than the width of the bottom layer of metallization (the return layer) then the structure would be known as a microstrip line rather than a parallel plate line. Other known transmission line structures may also be considered for implementing this device, e.g. co-planar lines, suspended stripline, etc. Support tube 364 may be a polypropylene tube having an outer diameter of 3.1 mm, and should be a good sliding fit inside a surgical endoscope with an inner diameter of 2.6 mm. This gives a wall thickness of about 0.25 mm. The material and thickness is not critical; nylon or polythene may be used, or a number of other plastics. The edges of the transmission line may be chamfered so that the probe will sit in place just below the diameter of the tube.

The tube comes 5 mm along the length of the transmission line 344. The overlap with the coaxial cable is 5 mm here but can be as long as required. The interface should preferably be chamfered, i.e. at an angle of 45°. The tube may be short enough to get through a bent endoscope. The main purpose of the tube is to support the probe and to hold it steady in the end of the endoscope. In practice, the tube may be up to or longer than 60 mm since it may be desirable for the instrument (the radiating blade) to protrude from the end of the instrument channel by up to or greater than 50 mm, whilst maintaining a degree of rigidity or strength as required to enable the radiating section to be pushed into tissue without bending or distorting. In some instances, the tube should not protrude at all from the end of the instrument channel as this may obscure vision and make it difficult to manipulate the instrument.

The mounting structure 368 and mounting blocks 366 may be made of almost any material that can be used to hold the structure in place, as this material does not affect the performance of the device if kept away from the probe edges and the pin of the coaxial cable.

The gap 362 between the upper conductive layer 358 and the coaxial cable is 0.5 mm. This gap is critical since it provides a static impedance match between the radiating portion of the probe and representative biological tissue in contact with the end section of the device radiating energy at the microwave frequency of choice, i.e. 5.8 GHz, into the tissue.

The centre of the probe is offset by about 0.5 mm (0.53 mm) from the centre of the coaxial cable. The axis of the outer tube is about 0.3 mm above the centre of the probe, but only needs to fit over the assembly and hold the components in place.

The dielectric sheet 368 may be just over one quarter or three quarters of a wavelength long at the frequency of operation (taking into account the loading caused by the dielectric material) so that a standing wave will not couple strongly to a supporting plastic tube near the base of the probe. This implies that the choice of material for tube is not critical in terms of its electrical performance, i.e. loss factor or dielectric constant. The length of the structure may be extended to any odd multiple of a quarter of the loaded wavelength at the frequency of interest.

Figure 14:
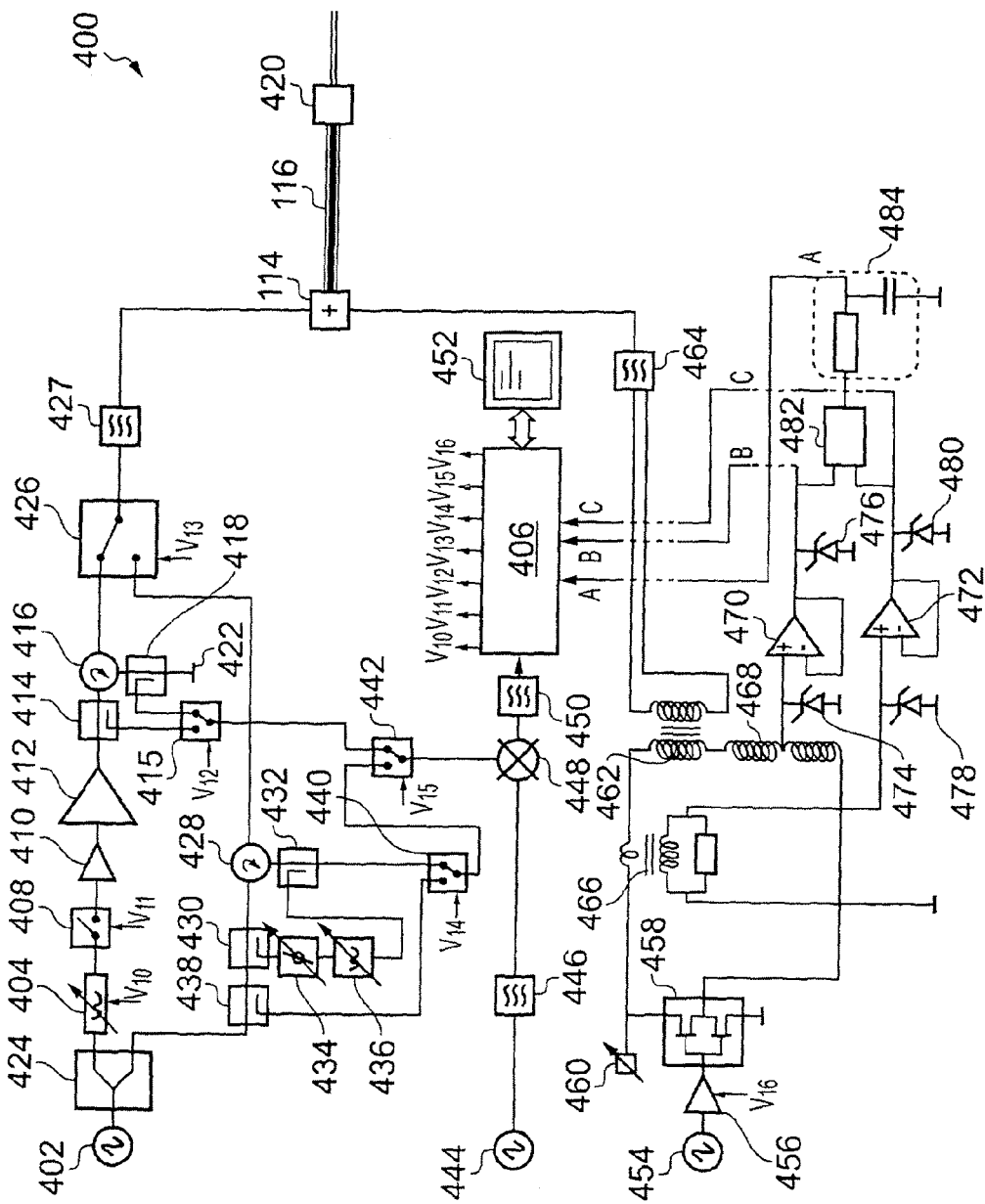
FIG. 14 is a schematic system diagram of electrosurgical apparatus according to an embodiment of the invention having a separate measurement channel.

FIG. 14 shows a complete system diagram for electrosurgical apparatus 400 according to an embodiment of the invention which has a separate measurement channel. In this embodiment, the microwave channel has a microwave frequency source 402, a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which is part of the microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection To create the measurement channel in this embodiment, a power splitter 424 (e.g. a 3 dB power splitter) is used to divide the signal from the source 402 into two branches. In an alternative embodiment, the power splitter 424 may be a omitted and a separate source used for the measurement channel. One branch from the power splitter 424 forms the microwave channel, and has the components described above connected thereon. The other branch forms the measurement channel. The measurement channel bypasses the amplifying line-up on the microwave channel, and hence is arranged to deliver a low power signal from the probe. In this embodiment, a primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel in this embodiment includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel.

The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. In the embodiment shown in FIG. 14 a single heterodyne receiver is used. A double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 14 comprises an RF frequency source 454 connected to a gate driver 456 that is controlled by the controller 406 via control signal $V_{16}$. The gate driver 456 supplies an operation signal for an RF amplifier 458, which in the embodiment is a half-bridge arrangement. The drain voltage of the half-bridge arrangement is controllable via a variable DC supply 460. An output transformer 462 transfers the generated RF signal on to a line for delivery to the probe 420. A low band pass filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. These mechanisms for measuring voltage and current are discussed above with reference to FIG. 4. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 14).

To derive phase information, the voltage and current signals (B and C) are also connected to a phase comparator 482 (e.g. an EXOR gate) whose output voltage is integrated by RC circuit 484 to produce a voltage output (shown as A in FIG. 14) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420 as discussed above with reference to FIG. 1.

Figure 15:
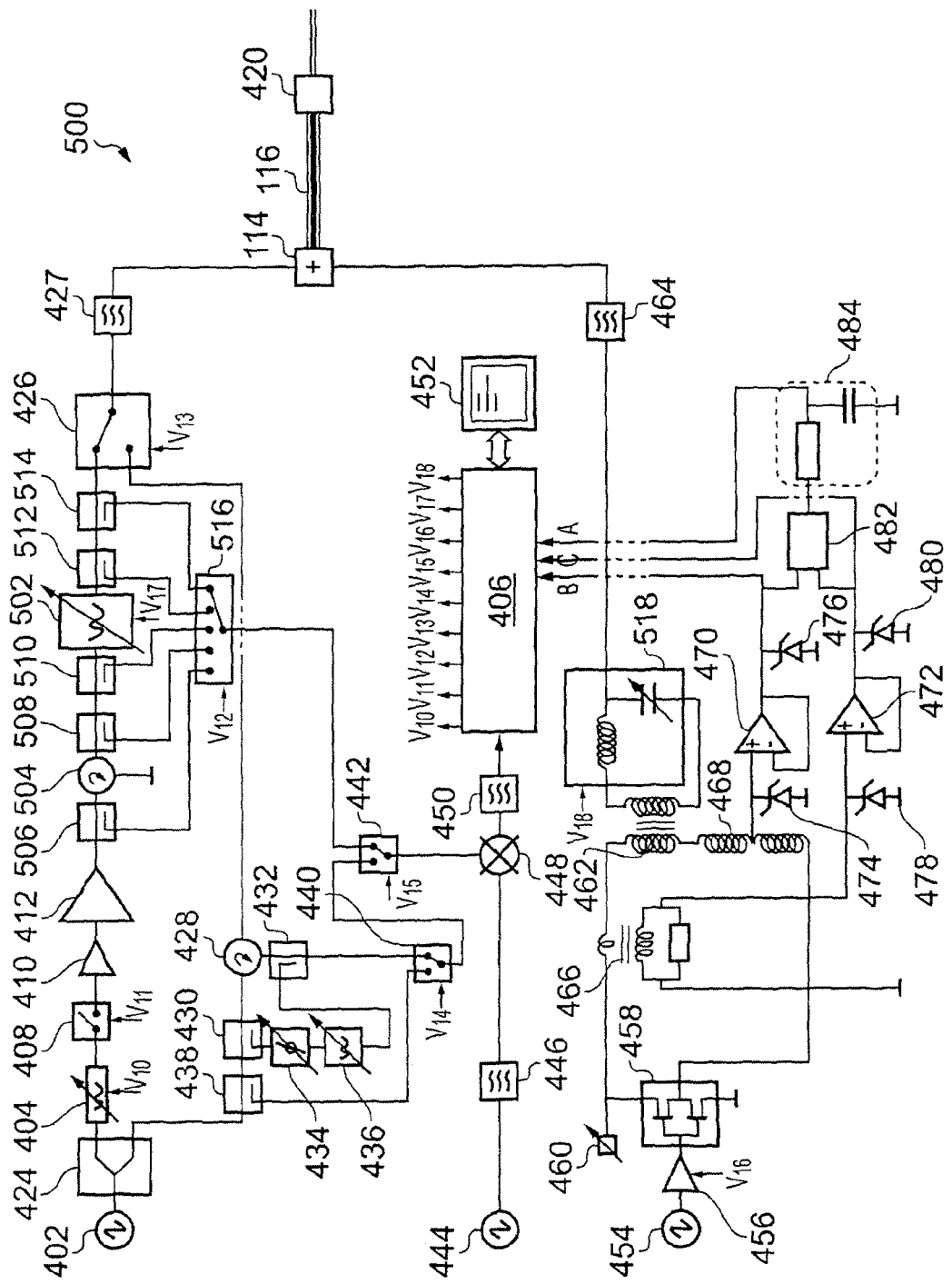
FIG. 15 is a schematic system diagram of electrosurgical apparatus according to an embodiment of the invention having a separate measurement channel and means for tuning on both the RF and microwave channels.

FIG. 15 shows a complete system diagram for electrosurgical apparatus 500 that is similar to the system shown in FIG. 14 but also includes components to match or tune the signals on the microwave and RF channels. Components in common between FIGS. 14 and 15 are given the same reference number and are not described again.

On the microwave channel an impedance adjuster 502 is connected between the amplifier module and probe. The impedance adjuster 502 is controlled by controller 406 via control signal $V_{17}$. A circulator 504 acts as an isolator between the amplifier module and impedance adjuster 502 to protect the power amplifier 412 from reflected signals. A forward coupler 506 connected between the power amplifier 412 and circulator 504 couples out a power amplifier monitoring signal. A forward coupler 508 and reflected coupler 510 are connected between the circulator 504 and impedance adjuster 502 to provide information about forward and reflected power signals on the microwave channel before the impedance adjuster 502. A forward coupler 512 and reflected coupler 514 are connected between impedance adjuster 502 and probe 420 to provide information about forward and reflected power signals on the microwave channel after the impedance adjuster 502. In combination, the couplers 508, 510, 512, 514 can extract information that permits the controller 406 to determine the power delivered from the probe and the power loss in the impedance adjustor 502. The latter is optional, so only one pair of couplers 512, 514 may be needed. A signal selection switch 516 operable by the controller 406 via control signal $V_{12}$ connects one of the outputs of the couplers 506, 508, 510, 512, 514 to the heterodyne receiver from where it is sent to the controller 406 to provide the microwave signal information.

On the RF channel, an RF tuning network 518 is connected to the secondary coil of the output transformer 462 and is operable by the controller 406 via control signal $V_{18}$. In this embodiment, the RF tuning network 518 comprises an adjustable series inductance and an adjustable shunt capacitance, e.g. a reverse of the arrangement discussed above with reference to FIG. 4.

Phase and magnitude information available from the RF and microwave channels can be used to control the variable elements contained within the RF tuning network 518 and impedance adjuster 502 to maximise the efficiency of energy delivery from both RF and microwave channels.

Figure 16:
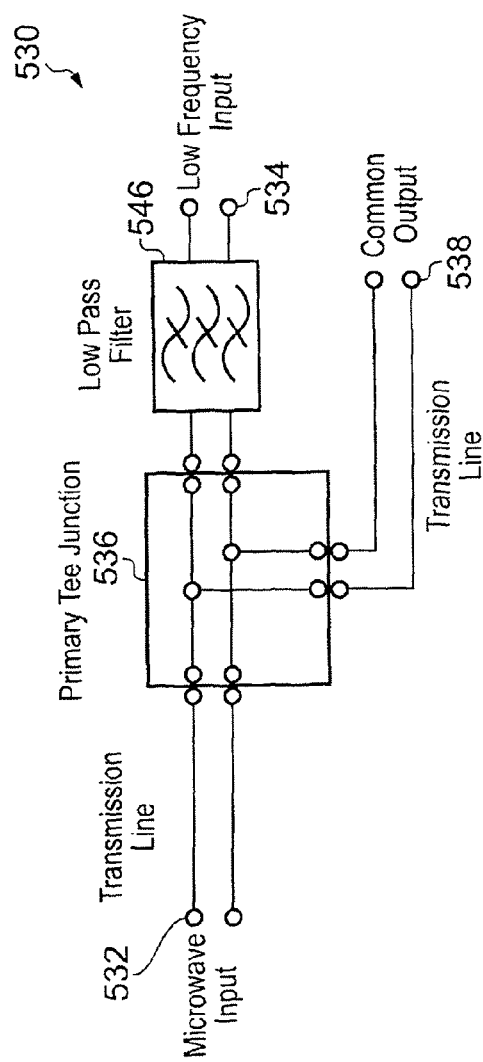
FIG. 16 is a schematic block diagram of a diplexer unit.

FIG. 16 is a block diagram illustrating a diplexer unit 530 for using as a signal combiner in the present invention. The diplexer unit 530 is to be constructed using circuitry in an 'open microstrip' configuration. Microwave EM radiation from the microwave channel enters the unit 530 at a first input port 532 and RF EM radiation from the RF channel enters the unit at a second input port 534. Respective transmission lines connect the first and second input ports to opposing input ports of a common (or primary) 'Tee' junction 536. The third (orthogonal) port of the primary Tee junction 536 is connected by a further transmission line to the output port 538 of the unit 530.

In the example shown in FIG. 16, the unit 530 has an integrally formed blocking filter 540 to isolate the microwave power the second input port. The blocking filter is effectively a 'low pass' filter, e.g. that is reflective at the frequency of the microwave EM radiation (e.g. 5.8 GHz) while allowing the lower frequency RF EM radiation (at e.g. 500 kHz) to pass. To ensure that the microwave signal experiences low transmission loss between the microwave input and the output port, the filter is positioned such that additional reactance is not added at the junction.

The circuit for the diplexer unit 530 may be printed onto a microwave quality substrate. A ceramic loaded PTFE based material (e.g. RT/duroid type 6006 which is manufactured by the Rogers Corporation) can be used for this purpose. The substrate thickness may be between 0.635 mm and 1.27 mm. To form the diplexer unit, the substrate material is coated with electrodeposited copper on both sides at a thickness of approximately 34 μm. This thickness can accommodate the high power levels required at the microwave frequency.

Figure 17:
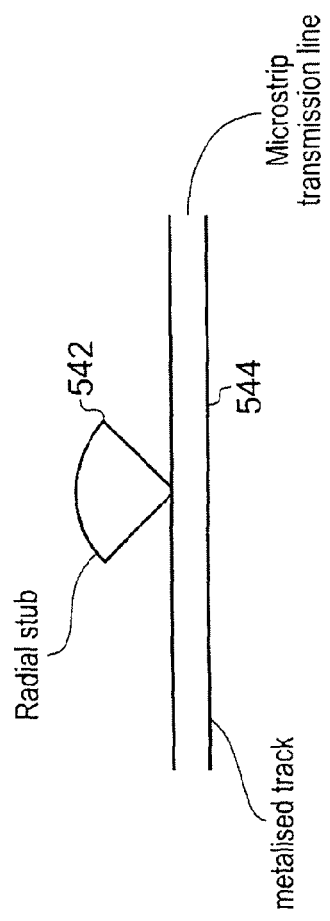
FIG. 17 is a diagram of a microstrip radial stub useful for the diplexer unit shown in FIG. 16.

To provide the function of the blocking filter, a circuit element having the configuration shown in FIG. 17 may be used. The topographical layout of this circuit element may be referred to as a 'radial stub'. It comprises a fan-shaped stub 542 connected in 'shunt' at is narrow base to a microstrip transmission line 544. With this configuration, the radial stub transforms an open circuit at its curved edge to a short circuit at the transmission line. Reflection of microwave power is therefore induced at the short circuit. The physical dimensions for the radial stub can be determined for a microwave frequency using known simulation techniques.

Figure 18:
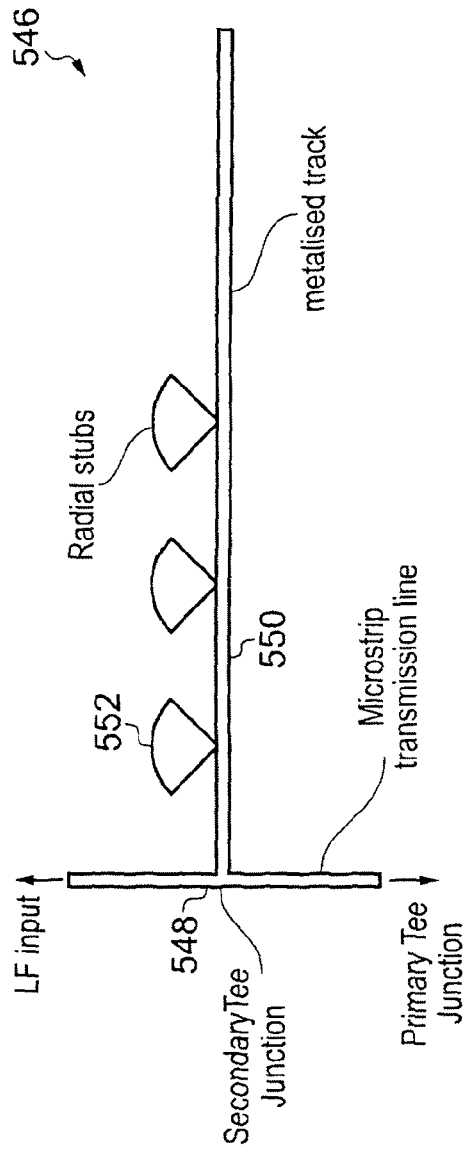
FIG. 18 is a topographical diagram showing the microstrip layout of a radial stub filter useful for the diplexer unit shown in FIG. 16.

FIG. 18 shows an example of a microstrip pattern 546 that may be used to implement the blocking filter. The microstrip pattern 546 comprises a secondary Tee junction 548 whose opposing inputs are connected between the low frequency input 534 and the primary Tee junction 536. The orthogonal input of the secondary Tee junction is connected to a microstrip transmission line 550 (i.e. metallised track) having three radial stubs are placed along the microstrip line between the Tee junction and the output port. Using more than one radial stub increasing isolation. The spacing between the adjacent radial stubs may be optimised using simulation techniques.

Figure 19:
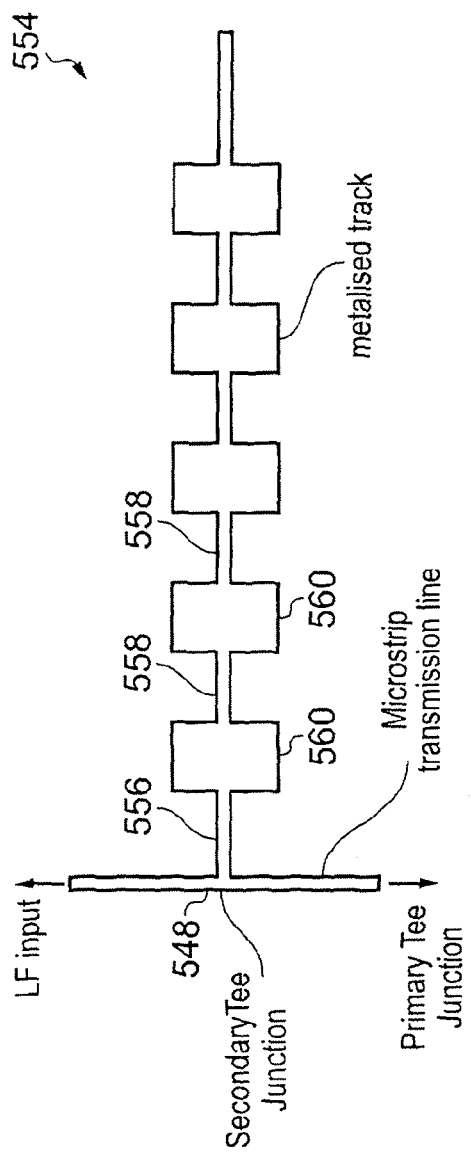
FIG. 19 is a topographical diagram showing the microstrip layout of a hi-lo impedance section filter useful for the diplexer unit shown in FIG. 16.

FIG. 19 shows an alternative microstrip pattern 554 for the blocking filter, where instead of the radial stubs a microstrip line 556 having a repetitive sequence of high impedance and low impedance sections is used. The high impedance sections 558 are characterised by a narrow transmission line, whereas the low impedance sections 560 are characterised by a wide transmission line.

Optionally, the microstrip diplexer unit may have a high pass filter integrally formed therewith. The high pass filter may function to block filter the RF EM radiation from the low frequency port 534 from passing into the microwave generator (i.e. leaking out of the microwave input 532). To provide this function, the microstrip pattern may comprise a rectangular stub in shunt with the microstrip transmission line between the microwave input 532 and the primary Tee junction 536. The end of the stub is to present a short circuit to the ground plane and the length of this stub is to be effectively a quarter of a guided wavelength at the frequency of the microwave EM radiation (e.g. 5.8 GHz). The result is that the short circuit impedance is transformed to an open circuit impedance at the position where the stub is connected to the edge of the microstrip transmission line.

The invention claimed is:

1. An electrosurgical apparatus for resection of biological tissue, the apparatus comprising:
a radiofrequency (RF) signal generator for generating RF electromagnetic (EM) radiation having a first frequency;
a microwave signal generator for generating microwave EM radiation having a second frequency that is higher than the first frequency;
a probe arranged to deliver the RF EM radiation and the microwave EM radiation separately or simultaneously from a distal end thereof;
a feed structure for conveying the RF EM radiation and the microwave EM radiation to the probe, the feed structure comprising an RF channel for connecting the probe to the RF signal generator, and a microwave channel for connecting the probe to the microwave signal generator;
an RF signal detector for sampling current and voltage on the RF channel and generating therefrom an RF detection signal ($S_{RF}$) indicative of the current and voltage;
a microwave signal detector for sampling forward and reflected power on the microwave channel and generating therefrom a microwave detection signal ($S_{M1}$, $S_{M2}$) indicative of the microwave power delivered by the probe; and
a controller in communication with the RF signal detector and microwave signal detector to receive the RF detection signal and the microwave detection signal,
wherein the controller is operable to select an energy delivery profile for the RF EM radiation and the microwave EM radiation, the energy delivery profile for the RF EM radiation being for tissue cutting and the energy delivery profile for the microwave EM radiation being for hemostasis or sealing or coagulation or ablation of tissue,
wherein the controller comprises a digital microprocessor programmed to output an RF control signal ($C_{RF}$) for the RF signal generator and a microwave control signal ($C_M$) for the microwave signal generator, the RF control signal and the microwave control signal being for setting the energy delivery profile for the RF EM radiation and the microwave EM radiation respectively, and
wherein the controller is arranged to determine a state for the RF control signal and the microwave control signal based on the received RF detection signal and the received microwave detection signal respectively.

2. The electrosurgical apparatus according to claim 1, wherein the feed structure includes a measurement channel for delivering energy at a power level of 10 mW or less.

3. The electrosurgical apparatus according to claim 2, wherein the measurement channel is connected to receive a measurement signal from the microwave signal generator, and wherein the electrosurgical apparatus is switchable so that microwave EM radiation is delivered to the probe either through the measurement channel or the microwave channel.

4. The electrosurgical apparatus according to claim 3, wherein the microwave signal detector includes a heterodyne or double heterodyne detector.

5. The electrosurgical apparatus according to claim 1, wherein, if the energy delivery profile for the RF EM radiation and/or the microwave EM radiation comprises a pulsed waveform, the electrosurgical apparatus is arranged to deliver energy to the probe along the measurement channel during an OFF time of the pulsed waveform.

6. The electrosurgical apparatus according to claim 1, wherein the controller is arranged to set the energy delivery profile of the RF EM radiation and the microwave EM radiation by adjusting the waveform and/or power of the RF EM radiation and the microwave EM radiation.

7. The electrosurgical apparatus according to claim 1, wherein the distal end of the probe comprises a bipolar emitting structure comprising a first conductor (358) spatially separated from a second conductor, the first and second conductors being arranged to act:
as an active electrode and a return electrode respectively to convey the RF EM radiation by conduction, and
as an antenna to radiate the microwave EM radiation.

8. The electrosurgical apparatus according to claim 7, including a gas feed connected to supply a flow of gas to the distal end of the probe, wherein, if the flow of gas is present, the RF EM radiation is controllable to strike a conducting gas plasma between the first conductor and the second conductor at the distal end of the probe and the microwave EM radiation is arranged to sustain the gas plasma.

9. The electrosurgical apparatus according to claim 7, wherein the bipolar emitting structure comprises a planar block of dielectric material, the first and second conductors being conductive layers provided on opposite surfaces of the planar block.

10. The electrosurgical apparatus according to claim 7, wherein the bipolar emitting structure comprises two opposing clamping surfaces for clamping biological tissue therebetween, the first conductor being provided on one of the clamping surfaces and the second conductor being provided on the other clamping surface.

11. The electrosurgical apparatus according to claim 1, wherein the RF channel and the microwave channel comprise physically separate signal pathways from the RF signal generator and the microwave signal generator respectively, the separate signal pathway on the RF channel being isolated from the microwave EM radiation and the separate signal pathway on the microwave channel being isolated from the RF EM radiation.

12. The electrosurgical apparatus according to claim 11, wherein the feed structure includes a combining circuit having a first input connected to the separate signal pathway on the RF channel, a second input connected to the separate signal pathway on the microwave channel, and an output connected to a common signal pathway for conveying the RF EM radiation and the microwave EM radiation separately or simultaneously along a single channel to the probe.

13. The electrosurgical apparatus according to claim 12, wherein the combining circuit includes a switching device for connecting either the RF channel or the microwave channel to the common signal pathway.

14. The electrosurgical apparatus according to claim 12, wherein the switching device comprises a relay or coaxial switch.

15. The electrosurgical apparatus according to claim 12, wherein the combining circuit comprises a bi-directional diplexer arranged to permit:
forward RF EM radiation to be conveyed from the first input to the output,
reflected RF EM radiation to be conveyed from the output to the first input,
forward microwave EM radiation to be conveyed from the second input to the output, and
reflected microwave EM radiation to be conveyed from the output to the second input.

16. The electrosurgical apparatus according to claim 15, wherein the bi-direction diplexer comprising a T-shaped open microstrip circuit having a low pass filter integrally formed therewith to prevent microwave EM radiation from leaking out of the first input.

17. The electrosurgical apparatus according to claim 1, wherein the RF detection signal from the RF signal detector is indicative of the voltage and the current of the RF EM radiation.

18. The electrosurgical apparatus according to claim 17, comprising an RF tuner connected on the RF channel for controlling the energy delivered into a tissue by the RF EM radiation, wherein the RF tuner has an adjustable reactance that is controllable by the controller based on the RF detection signal.

19. The electrosurgical apparatus according to claim 18, wherein the adjustable reactance of the RF tuner comprises a plurality of reactive elements, each reactive element having a fixed reactance and being independently switchable into or out of connection with the RF channel according to a respective control signal from the controller.

20. The electrosurgical apparatus according to claim 18, wherein the adjustable reactance of the RF tuner comprises a plurality of reactive elements, each reactive element having a variable reactance that is independently controllable according to a respective control signal from the controller.

21. The electrosurgical apparatus according to claim 18, wherein the adjustable reactance of the RF tuner is provided by a variable capacitor or a variable inductor, and the controller comprises a self-adjusting feedback loop arranged to generate a signal for setting the reactance of the variable capacitor or the variable inductor.

22. The electrosurgical apparatus according to claim 18, wherein the adjustable reactance of the RF tuner is provided by a variable capacitor and a variable inductor, and the controller comprises a self-adjusting feedback loop arranged to generate a signal for setting the reactance of the variable capacitor and the variable inductor.

23. The electrosurgical apparatus according to claim 1, wherein the microwave detection signal is indicative of the magnitude of reflected microwave power on the microwave channel.

24. The electrosurgical apparatus according to claim 23, including an impedance adjuster connected on the microwave channel between the microwave signal generator and the probe, the impedance adjuster having an adjustable complex impedance that is controllable by the controller based on the microwave detection signal.

25. The electrosurgical apparatus according to claim 1, wherein the RF signal generator comprises:
an oscillator coupled to a switching unit (or generating a stable RF output;
an amplifier for amplifying the stable RF output; and
an output transformer,
wherein the amplifier is arranged to amplify a voltage across a primary coil of the output transformer, and the switching unit is arranged to switch ON/OFF a voltage across the primary coil of the output transformer.

26. The electrosurgical apparatus according to claim 1, wherein the first frequency is a stable fixed frequency in the range 10 kHz to 300 MHz and the second frequency is a stable fixed frequency in the range 300 MHz to 100 GHz.

27. The electrosurgical apparatus according to claim 1, for use in a clinical procedure relating to any one of Natural Orifice Transluminal Endoscopic Surgery (NOTES), Transanal Endoscopic Microsurgery (TEMS), and single port laparoscopic surgery.

* * * * *